United States Patent
Kyushima et al.

(10) Patent No.: US 10,225,491 B2
(45) Date of Patent: Mar. 5, 2019

(54) SOLID-STATE IMAGING DEVICE, X-RAY IMAGING SYSTEM, AND SOLID-STATE IMAGING DEVICE DRIVING METHOD

(71) Applicant: HAMAMATSU PHOTONICS K.K., Hamamatsu-shi, Shizuoka (JP)

(72) Inventors: Ryuji Kyushima, Hamamatsu (JP); Kazuki Fujita, Hamamatsu (JP); Haruyoshi Okada, Hamamatsu (JP); Junichi Sawada, Hamamatsu (JP); Harumichi Mori, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 146 days.

(21) Appl. No.: 15/325,729

(22) PCT Filed: Jul. 9, 2015

(86) PCT No.: PCT/JP2015/069763
§ 371 (c)(1),
(2) Date: Jan. 12, 2017

(87) PCT Pub. No.: WO2016/009940
PCT Pub. Date: Jan. 21, 2016

(65) Prior Publication Data
US 2017/0187967 A1    Jun. 29, 2017

(30) Foreign Application Priority Data
Jul. 16, 2014 (JP) .................................. 2014-145612

(51) Int. Cl.
*H04N 5/00* (2011.01)
*H04N 5/32* (2006.01)
(Continued)

(52) U.S. Cl.
CPC ............. *H04N 5/32* (2013.01); *G01N 23/046* (2013.01); *H04N 5/347* (2013.01); *H04N 5/378* (2013.01)

(58) Field of Classification Search
CPC ...................................................... H04N 5/347
See application file for complete search history.

(56) References Cited

U.S. PATENT DOCUMENTS 5,436,893 A    7/1995   Barnett
2001/0021030 A1  9/2001   Ohshita
(Continued)

FOREIGN PATENT DOCUMENTS

CN    102017609 A    4/2011
CN    102590844 A    7/2012
(Continued)

OTHER PUBLICATIONS

International Preliminary Report on Patentability dated Jan. 26, 2017 for PCT/JP2015/069763.

*Primary Examiner* — Dani Fox
(74) *Attorney, Agent, or Firm* — Drinker Biddle & Reath LLP

(57) ABSTRACT

A solid-state imaging device includes a photodetecting unit including MN pixels arrayed two-dimensionally in M rows and N columns, an output unit outputting a digital value generated on the basis of the amount of charge input from the pixels, and a control unit. The control unit divides the MN pixels in the photodetecting unit into unit regions each including pixels in Q rows and R columns, divides the unit regions arrayed two-dimensionally in (M/Q) rows and (N/R) columns into binning regions each including unit regions in K rows and one column, and repeatedly outputs the digital value according to the sum of amounts of the charges output from KQR pixels included in each binning region from the output unit K times in a column order for each row sequen-
(Continued)

tially for the binning regions arrayed two-dimensionally in (M/KQ) rows and (N/R) columns.

11 Claims, 14 Drawing Sheets

(51) Int. Cl.
    *H04N 5/347*     (2011.01)
    *H04N 5/378*     (2011.01)
    *G01N 23/046*     (2018.01)

(56) References Cited

U.S. PATENT DOCUMENTS

| | | |
|---|---|---|
| 2010/0208113 A1 | 8/2010 | Kyushima et al. |
| 2011/0064195 A1* | 3/2011 | Kyushima .............. A61B 6/032 378/62 |
| 2011/0135057 A1 | 6/2011 | Mori et al. |
| 2011/0141255 A1 | 6/2011 | Mori et al. |
| 2011/0267495 A1 | 11/2011 | Atkinson |
| 2013/0086360 A1 | 4/2013 | Zeng et al. |
| 2013/0193334 A1 | 8/2013 | Dowaki |
| 2014/0071271 A1 | 3/2014 | Altmann |

FOREIGN PATENT DOCUMENTS

| | | |
|---|---|---|
| CN | 103314573 A | 9/2013 |
| JP | 2006-314774 A | 11/2006 |
| JP | 2008-060981 A | 3/2008 |
| JP | 2011-030181 A | 2/2011 |
| JP | 2012-151551 A | 8/2012 |
| JP | 2012-182836 A | 9/2012 |
| JP | 2013-126169 A | 6/2013 |
| WO | WO 2011/023229 A1 | 3/2011 |

* cited by examiner

SOLID-STATE IMAGING DEVICE, X-RAY IMAGING SYSTEM, AND SOLID-STATE IMAGING DEVICE DRIVING METHOD

TECHNICAL FIELD

The present invention relates to a solid-state imaging device, an X-ray imaging system including the solid-state imaging device, and a method of driving the solid-state imaging device.

BACKGROUND ART

As a solid-state imaging device, a device using CMOS technology is known, and particularly, a device using a passive pixel sensor (PPS) configuration is known. The solid-state imaging device of the PPS configuration includes a photodetecting unit in which PPS type pixels each including a photodiode that generates a charge of an amount according to an incident light intensity are arrayed two-dimensionally in M rows and N columns. This solid-state imaging device outputs a voltage value according to the amount of the charge generated in the photodiode according to light incidence in each pixel.

In general, an output terminal of each of M pixels in each column is connected to an input terminal of an integration circuit provided corresponding to the column via a readout line provided corresponding to the column. In each row sequentially from a first row to an M-th row, a charge generated in the photodiode of the pixel is input to the corresponding integration circuit via the corresponding readout line, and the voltage value according to the amount of charge is output from the integration circuit. Further, this voltage value is subjected to AD conversion to be a digital value.

The solid-state imaging device of the PPS configuration is used in various applications, for example, the device is used as an X-ray flat panel in medical applications or industrial applications in combination with a scintillator unit, and more specifically, the device is used in an X-ray CT apparatus, a microfocus X-ray inspection apparatus, or the like. An X-ray imaging system disclosed in Patent Document 1 can image X-rays output from an X-ray generating device and transmitted through an imaging object using a solid-state imaging device and image the imaging object. This X-ray imaging system can image X-rays transmitted through the imaging object in imaging modes of a plurality of types using the solid-state imaging device.

CITATION LIST

Patent Literature

Patent Document 1: Japanese Patent Application Laid-Open Publication No. 2006-314774

SUMMARY OF INVENTION

Technical Problem

In such a solid-state imaging device, improvement of S/N ratio and improvement of frame rate are required. Imaging may be performed while moving the solid-state imaging device in some applications or imaging modes, and in the solid-state imaging device used in such a case, improvement of S/N ratio and improvement of frame rate are expected due to a shape of the photodiode of each pixel that is long in a movement direction.

For example, in a panoramic imaging mode or a CT imaging mode, imaging is performed while moving the solid-state imaging device, and a signal obtained by the imaging is processed so that an image of an imaging object is reconstructed. In this case, a movement distance of the solid-state imaging device in an imaging period of one frame may be several mm. The amount of charge output from each pixel corresponds to an integrated value of the amount of incident light over a movement distance per frame.

Therefore, even when the photodiode of each pixel of the solid-state imaging device is elongated in a movement direction, degradation of quality of an image obtained through a reconstruction process is small. Instead, improvement of an S/N ratio can be expected if the amount of light incident on each pixel increases due to an increase in an area of the photodiode of each pixel, and improvement of a frame rate can also be expected due to a decrease in the number of pixels.

However, in an actual system using a solid-state imaging device, there are various movement speeds of the solid-state imaging device, and design of a length in a movement direction of the photodiode of each pixel of the solid-state imaging device for each system is not practical. Further, it may not be preferable for the photodiode of each pixel of the solid-state imaging device to have a shape that is long in the movement direction according to imaging modes.

A technology capable of obtaining the same effects as those when a shape of the photodiode of each pixel is long in the movement direction includes binning in which a value obtained by adding output values from a plurality of pixels included in a region is set to a value of the region. In this technology, it is possible to flexibly set a shape or a size of a binning region in units of pixels.

When binning of the conventional art is applied to a solid-state imaging device including a photodetecting unit in which MN pixels are arrayed two-dimensionally in M rows and N columns and, for example, binning regions each including pixels in two rows and one column are assumed, signals with the number of data corresponding to (M/2) rows and N columns per frame are output from the solid-state imaging device. That is, when binning is performed, the number of data of the output signals per frame becomes ½, and the frame rate can be doubled in comparison with the case of no binning. Further, an S/N ratio is also improved.

In the conventional art, the number of data of the output signals per frame decreases by performing binning, and further, the number of data of the output signals per frame is different due to the number of pixels included in each binning region. When the number of data of the output signals per frame is different, it is necessary for contents of an image reconstruction process to be changed according thereto. Thus, the output signal is not easy to handle in the binning of the conventional art.

The present invention has been made to solve the above problem, and an object thereof is to provide a solid-state imaging device capable of outputting a signal that is easy to handle even when binning is performed, and an X-ray imaging system including such a solid-state imaging device. Another object of the present invention is to provide a method of driving a solid-state imaging device so that a signal that is easy to handle can be output even when binning is performed.

Solution to Problem

A solid-state imaging device according to the present invention includes: (1) a photodetecting unit including MN pixels $P_{1,1}$ to $P_{M,N}$, each including a photodiode generating a charge of an amount according to an incident light intensity and a readout switch connected to the photodiode, arrayed two-dimensionally in M rows and N columns; (2) a row selection line $L_{V,m}$ applying an m-th row selection control signal for instructing an opening and closing operation to the readout switch of each of N pixels $P_{m,1}$ to $P_{m,N}$ in an m-th row in the photodetecting unit; (3) a readout line $L_{O,n}$ being connected to the readout switch of each of M pixels $P_{1,n}$ to $P_{M,n}$ in an n-th column in the photodetecting unit, and reading the charge generated in the photodiode of any of the M pixels $P_{1,n}$ to $P_{M,n}$ via the readout switch of the pixel; (4) an output unit being connected to each of the readout lines $L_{O,1}$ to $L_{O,N}$ and outputting a digital value generated on the basis of the amount of the charge input via the readout line $L_{O,n}$; and (5) a control unit controlling an opening and closing operation of the readout switch of each of MN pixels $P_{1,1}$ to $P_{M,N}$ in the photodetecting unit via the row selection lines $L_{V,1}$ to $L_{V,M}$ and controlling a digital value output operation in the output unit.

Further, in the solid-state imaging device, the control unit divides the pixels $P_{1,1}$ to $P_{M,N}$ arrayed two-dimensionally in M rows and N columns in the photodetecting unit into unit regions each including pixels in Q rows and R columns, divides the unit regions arrayed two-dimensionally in (M/Q) rows and (N/R) columns into binning regions each including unit regions in K rows and one column, closes the readout switches of the pixels included in the binning region in the row for each row sequentially for the binning regions arrayed two-dimensionally in (M/KQ) rows and (N/R) columns in the photodetecting unit, inputs the charges generated in the photodiodes of the pixels to the output unit, and repeatedly outputs the digital value according to the sum of amounts of the charges output from the KQR pixels included in each binning region from the output unit K times sequentially for each column. Here, M and N are each an integer of 2 or more, m is an integer of 1 or more and M or less, n is an integer of 1 or more and N or less, Q and R are each an integer of 1 or more, and K is an integer of 2 or more.

An X-ray imaging system according to the present invention includes the solid-state imaging device of the above configuration, and an X-ray generating device, and X-rays output from the X-ray generating device and transmitted through an imaging object are imaged by the solid-state imaging device.

A solid-state imaging device driving method according to the present invention is a method for driving a solid-state imaging device including the photodetecting unit, the row selection line $L_{V,m}$, the readout line $L_{O,n}$, and the output unit of the above configuration, and the method includes: dividing the pixels $P_{1,1}$ to $P_{M,N}$ arrayed two-dimensionally in M rows and N columns in the photodetecting unit into unit regions each including pixels in Q rows and R columns, dividing the unit regions arrayed two-dimensionally in (M/Q) rows and (N/R) columns into binning regions each including unit regions in K rows and one column, closing the readout switches of the pixels included in the binning region in the row for each row sequentially for the binning regions arrayed two-dimensionally in (M/KQ) rows and (N/R) columns in the photodetecting unit, inputting the charges generated in the photodiodes of the pixels to the output unit, and repeatedly outputting the digital value according to the sum of amounts of the charges output from the KQR pixels included in each binning region from the output unit K times sequentially for each column. Here, M and N are each an integer of 2 or more, m is an integer of 1 or more and M or less, n is an integer of 1 or more and N or less, Q and R are each an integer of 1 or more, and K is an integer of 2 or more.

Advantageous Effects of Invention

According to the present invention, in the solid-state imaging device, it is possible to output a signal that is easy to handle even when binning is performed.

DESCRIPTION OF EMBODIMENTS

Hereinafter, embodiments of the present invention will be described in detail with reference to the accompanying drawings. In the description of the drawings, the same elements will be denoted by the same reference signs, without redundant description.

Figure 1:
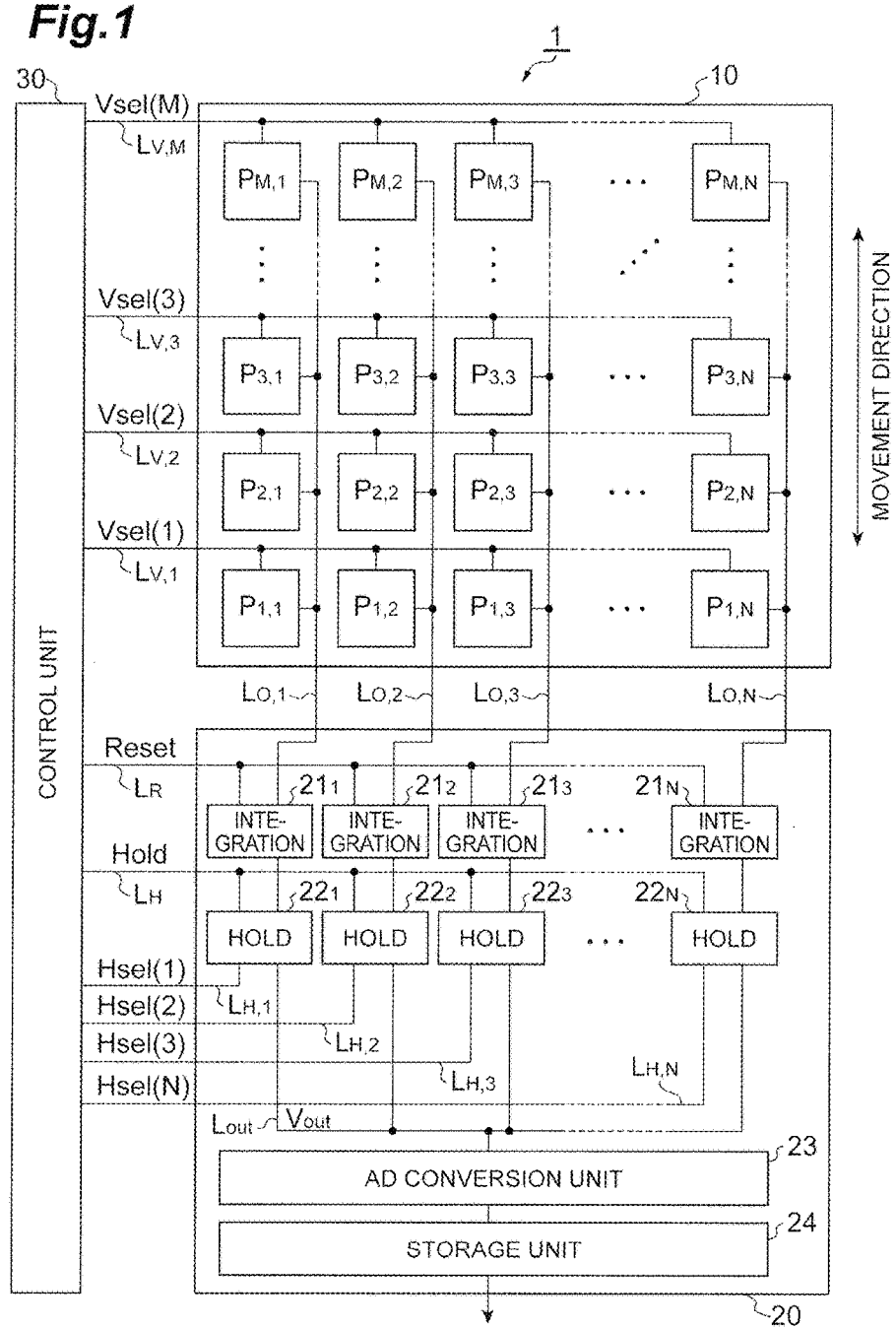
FIG. 1 is a diagram illustrating a configuration of a solid-state imaging device 1 of a first embodiment.

FIG. 1 is a diagram illustrating a configuration of a solid-state imaging device 1 of a first embodiment. The solid-state imaging device 1 includes a photodetecting unit 10, an output unit 20, and a control unit 30. When the solid-state imaging device 1 is used for X-ray imaging, it is preferable for the solid-state imaging device to include a scintillator unit covering the photodetecting unit 10.

In the photodetecting unit 10, MN pixels $P_{1,1}$ to $P_{M,N}$ are two-dimensionally arrayed in M rows and N columns. The MN pixels $P_{1,1}$ to $P_{M,N}$ are arranged with a constant pitch in both of the row and column directions. The pixel $P_{m,n}$ is located in an m-th row and an n-th column. Each pixel $P_{m,n}$ uses a PPS configuration and has the same configuration. Each of N pixels $P_{m,1}$ to $P_{m,N}$ in the m-th row is connected to the control unit 30 by an m-th row selection line $L_{V,m}$. An output terminal of each of the M pixels $P_{1,n}$ to $P_{M,n}$ in the n-th column is connected to the output unit 20 by the n-th column readout line $L_{V,m}$. Here, each of M and N is an integer of 2 or more, m is an integer of 1 or more and M or less, and n is an integer of 1 or more and N or less.

The output unit 20 outputs a digital value generated on the basis of the amount of charge input via the readout line $L_{O,n}$. The output unit 20 includes N integration circuits $21_1$ to $21_N$, N hold circuits $22_1$ to $22_N$, an AD conversion unit 23, and a storage unit 24. Each integration circuit $21_n$ has the same configuration. Each hold circuit $22_n$ has the same configuration.

Each integration circuit $21_n$ accumulates charge input to the input terminal via any column readout line, and outputs a voltage value according to the accumulated charge amount from an output terminal to the hold circuit $22_n$. Although each integration circuit $21_n$ is connected to the n-th column readout line $L_{O,n}$ in FIG. 1, the integration circuit may be connected to another readout line by a switch, as described later. Each of the N integration circuits $21_1$ to $21_N$ is connected to the control unit 30 by a reset line $L_R$.

Each hold circuit $22_n$ includes an input terminal connected to the output terminal of the integration circuit $21_n$, holds a voltage value input to this input terminal, and outputs the held voltage value from an output terminal to the AD conversion unit 23. Each of the N hold circuits $22_1$ to $22_N$ is connected to the control unit 30 by a hold line $L_H$. Further, each hold circuit $22_n$ is connected to the control unit 30 by an n-th column selection line $L_{H,n}$.

The AD conversion unit 23 receives the voltage value output from each of the N hold circuits $22_1$ to $22_N$, performs an AD conversion process on the input voltage value (analog value), and outputs a digital value according to the input voltage value to the storage unit 24. The storage unit 24 receives and stores the digital values output from the AD conversion unit 23, and sequentially outputs the stored digital values.

The control unit 30 outputs an m-th row selection control signal Vsel(m) to the m-th row selection line $L_{V,m}$ to apply this m-th row selection control signal Vsel(m) to each of the N pixels $P_{m,1}$ to $P_{m,N}$ of the m-th row. The control unit 30 outputs a reset control signal Reset to the reset line $L_R$ to apply this reset control signal Reset to each of the N integration circuits $21_1$ to $21_N$. The control unit 30 outputs a hold control signal Hold to the hold line $L_H$ to apply this hold control signal Hold to each of the N hold circuits $22_1$ to $22_N$. The control unit 30 outputs an n-th column selection control signal Hsel(n) to the n-th column selection line $L_{H,n}$ to apply this n-th column selection control signal Hsel(n) to the hold circuit $22_n$. Further, the control unit 30 controls the AD conversion process in the AD conversion unit 23 and controls writing and reading of the digital value in the storage unit 24.

Figure 2:
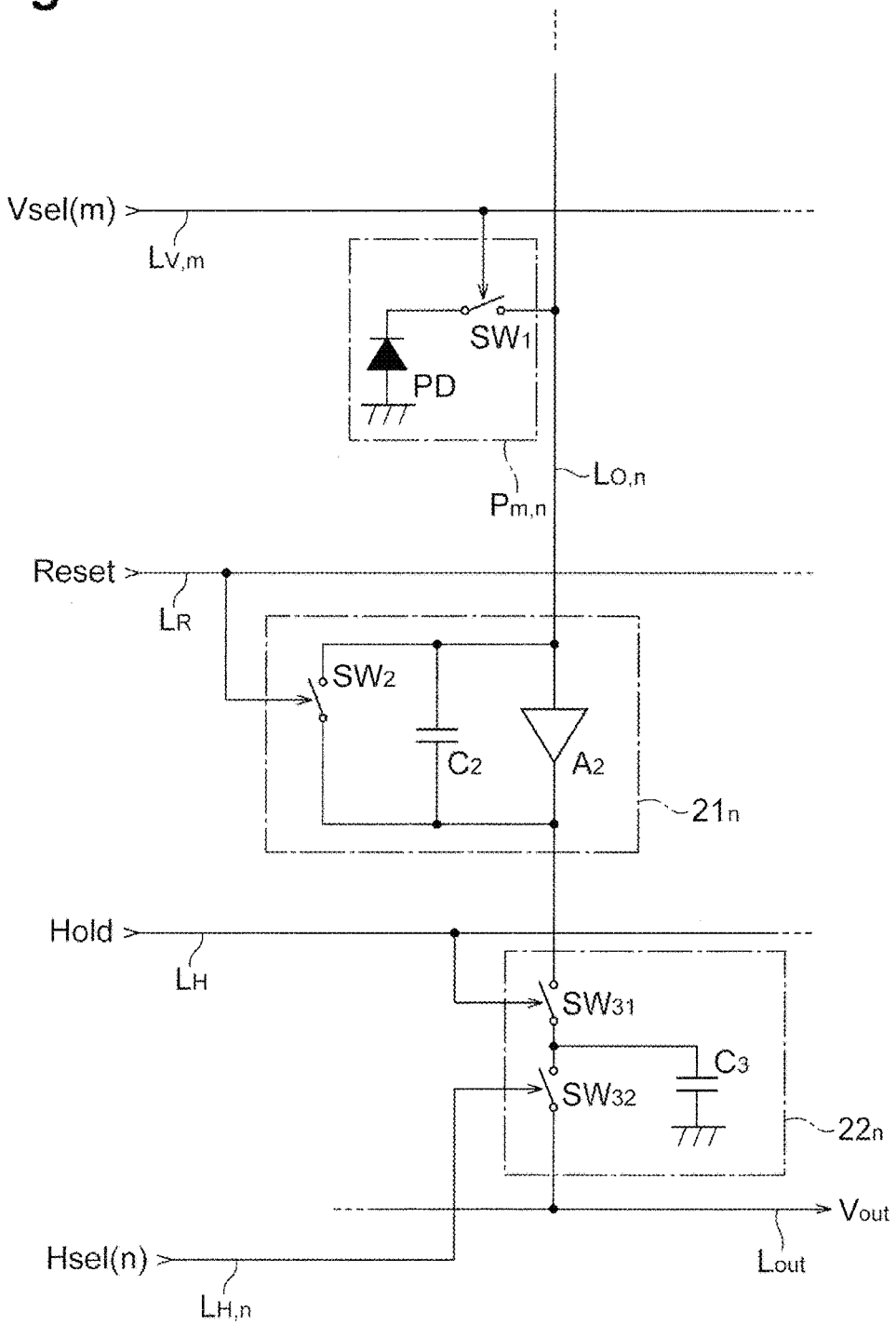
FIG. 2 is a circuit diagram of each of a pixel $P_{m,n}$, an integration circuit $21_n$, and a hold circuit $22_n$ of the solid-state imaging device 1.

FIG. 2 is a circuit diagram of each of the pixel $P_{m,n}$, the integration circuit $21_n$, and the hold circuit $22_n$ of the solid-state imaging device 1. Here, a circuit diagram of the pixel $P_{m,n}$ as a representative of the MN pixels $P_{1,1}$ to $P_{M,N}$ is illustrated, a circuit diagram of the integration circuit $21_n$ as a representative of the N integration circuits $21_1$ to $21_N$ is illustrated, and a circuit diagram of the hold circuit $22_n$ as a representative of the N hold circuits $22_1$ to $22_N$ is illustrated. That is, a circuit portion related to the pixel $P_{m,n}$ of the m-th row and the n-th column and the n-th column readout line $L_{O,n}$ is illustrated.

The pixel $P_{m,n}$ includes a photodiode PD and a readout switch $SW_1$. An anode terminal of the photodiode PD is grounded, and a cathode terminal of the photodiode PD is connected to the n-th column readout line $L_{O,n}$ via the readout switch $SW_1$. The photodiode PD generates charge of the amount according to an incident light intensity and accumulates the generated charge in a junction capacitance portion. A shape of a photosensitive region of the photodiode PD is preferably substantially a square. The m-th row selection control signal Vsel(m) passing through the m-th row selection line $L_{V,m}$ from the control unit 30 is applied to the readout switch $SW_1$. The m-th row selection control signal Vsel(m) is intended to instruct an opening and closing operation of the readout switch $SW_1$ of each of the N pixels $P_{m,1}$ to $P_{m,N}$ in the m-th row in the photodetecting unit 10.

In this pixel $P_{m,n}$, when the m-th row selection control signal Vsel(m) is at a low level, the readout switch $SW_1$ is opened, and the charge generated in the photodiode PD is accumulated in the junction capacitance portion without being output to the n-th column readout line $L_{O,n}$. On the other hand, when the m-th row selection control signal Vsel(m) is at a high level, the readout switch $SW_1$ is closed, and the charge generated in the photodiode PD and accumulated in the junction capacitance portion until then is output to the n-th column readout line $L_{O,n}$ via the readout switch $SW_1$.

The n-th column readout line $L_{O,n}$ is connected to the readout switch $SW_1$ of each of the M pixels $P_{1,n}$ to $P_{M,n}$ in the n-th column in the photodetecting unit 10. The n-th column readout line $L_{O,n}$ reads the charge generated in the photodiode PD of any of the M pixels $P_{1,n}$ to $P_{M,n}$ via the readout switch SW1 of the pixel, and transfers the charge to the integration circuit $21_n$.

The integration circuit $21_n$ includes an amplifier $A_2$, an integration capacitive element $C_2$, and a reset switch $SW_2$. The integration capacitive element $C_2$ and the reset switch $SW_2$ are connected in parallel to each other, and are provided between an input terminal and an output terminal of the amplifier $A_2$. The input terminal of the amplifier $A_2$ is connected to the n-th column readout line $L_{O,n}$. The reset control signal Reset passing through the reset line $L_R$ from the control unit 30 is applied to the reset switch $SW_2$. The reset control signal Reset is intended to instruct an opening and closing operation of the reset switch $SW_2$ of each of the N integration circuits $21_1$ to $21_N$.

In this integration circuit $21_n$, when the reset control signal Reset is at a high level, the reset switch $SW_2$ is closed, the integration capacitive element $C_2$ is discharged, and the voltage value output from the integration circuit $21_n$ is reset. On the other hand, when the reset control signal Reset is at a low level, the reset switch $SW_2$ is opened, the charge input to the input terminal is accumulated in the integration capacitive element $C_2$, and the voltage value according to the accumulated charge amount is output from the integration circuit $21_n$.

The hold circuit $22_n$ includes an input switch $SW_{31}$, an output switch $SW_{32}$, and a hold capacitive element $C_3$. One terminal of the hold capacitive element $C_3$ is grounded. The other terminal of the hold capacitive element $C_3$ is connected to an output terminal of the integration circuit $21_n$ via the input switch $SW_{31}$, and is connected to a voltage output line $L_{out}$ via the output switch $SW_{32}$. The hold control signal Hold passing through the hold line $L_H$ from the control unit 30 is applied to the input switch $SW_{31}$. The hold control signal Hold is intended to instruct an opening and closing operation of the input switch $SW_{31}$ of each of the N hold circuits $22_1$ to $22_N$. The n-th column selection control signal Hsel(n) passing through the n-th column selection line $L_{H,n}$ from the control unit 30 is applied to the output switch $SW_{32}$. The n-th column selection control signal Hsel(n) is intended to instruct an opening and closing operation of the output switch $SW_{32}$ of the hold circuit $22_n$.

In this hold circuit $22_n$, when the hold control signal Hold is changed from a high level to a low level, the input switch $SW_{31}$ is changed from a closed state to an open state, and the voltage value input to the input terminal at that time is held in the hold capacitive element $C_3$. When the n-th column selection control signal Hsel(n) is at a high level, the output switch $SW_{32}$ is closed and the voltage value held in the hold capacitive element $C_3$ is output to the voltage output line $L_{out}$.

The control unit 30 performs the following control when outputting a voltage value according to a detected light intensity of the pixel $P_{m,n}$. The control unit 30 instructs the reset switch $SW_2$ of the integration circuit $21_n$ to be closed using the reset control signal Reset so that the integration capacitive element $C_2$ of the integration circuit $21_n$ is discharged. After the discharging, the control unit 30 instructs the reset switch $SW_2$ of the integration circuit $21_n$ to be opened using the reset control signal Reset so that the integration capacitive element $C_2$ of the integration circuit $21_n$ can accumulate charge, and then instructs the readout switch $SW_1$ of the pixel $P_{m,n}$ to be closed during a predetermined period of time using the m-th row selection control signal Vsel(m) so that charge accumulated in the junction capacitance portion of the photodiode PD of the pixel $P_{m,n}$ is input to the integration circuit $21_n$.

The control unit 30 instructs the input switch $SW_{31}$ of the hold circuit $22_n$ to be changed from a closed state to an open state using the hold control signal Hold in the predetermined period of time so that the voltage value output from the integration circuit $21_n$ is held in the hold capacitive element $C_3$ of the hold circuit $22_n$. After the predetermined period of time, the control unit 30 instructs the output switch $SW_{32}$ of the hold circuit $22_n$ to be closed during a certain period of time using the column selection control signal Hsel(n) so that the voltage value held in the hold capacitive element $C_3$ of the hold circuit $22_n$ is output to the voltage output line $L_{out}$.

Further, the control unit 30 causes the AD conversion unit 23 to AD convert the voltage value output from the hold circuit $22_n$ to the voltage output line $L_{out}$, and stores a digital value output from the AD conversion unit 23 in the storage unit 24. The control unit 30 controls a digital value output operation from the storage unit 24.

Figure 3:
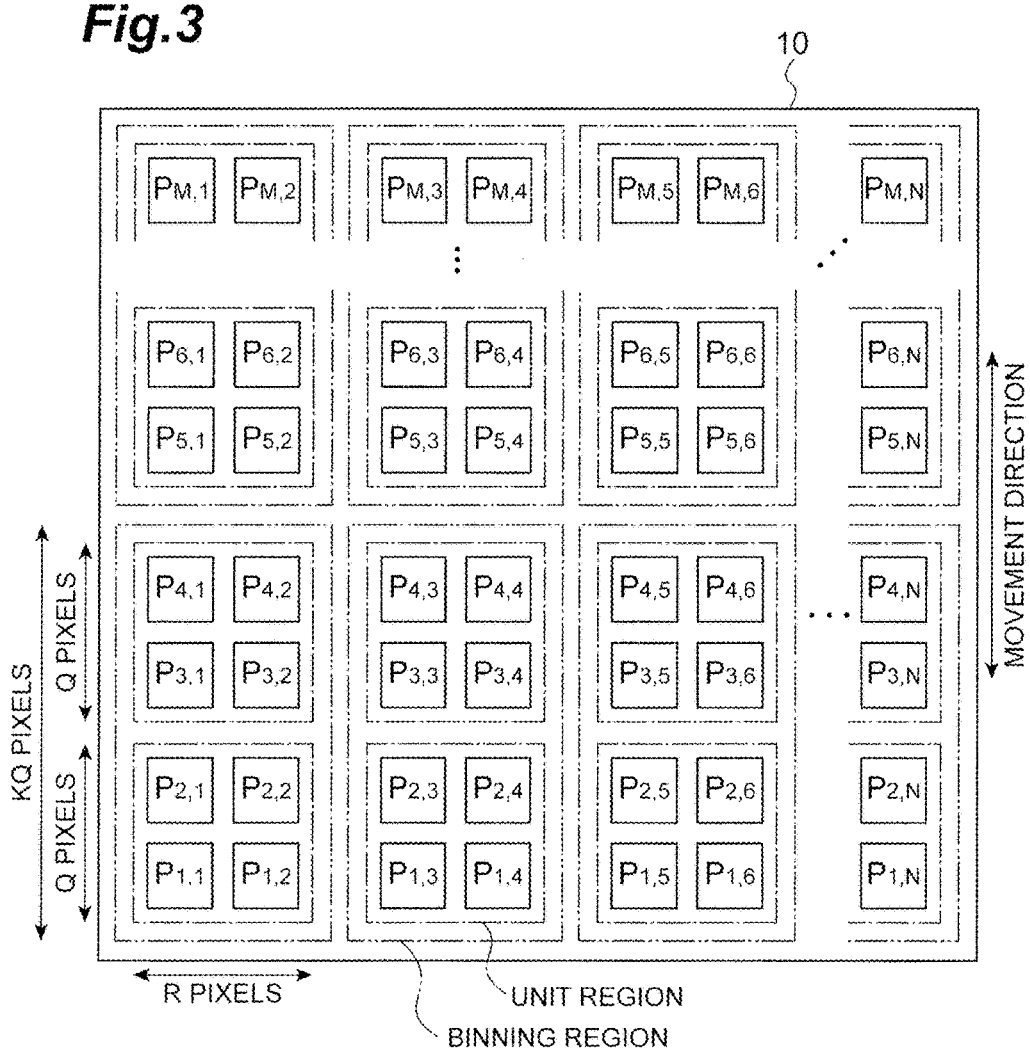
FIG. 3 is a diagram illustrating a unit region and a binning region in a photodetecting unit 10 of the solid-state imaging device 1.

FIG. 3 is a diagram illustrating a unit region and a binning region in the photodetecting unit 10 of the solid-state imaging device 1. The solid-state imaging device 1 can output a digital value according to an incident light intensity of each pixel $P_{m,n}$ under the control of the control unit 30, and in addition, output a digital value according to the sum of the incident light intensities of the pixels included in each unit region, and output a digital value according to the sum of the incident light intensities of the pixels included in each binning region.

The unit region is obtained by dividing the MN pixels $P_{1,1}$ to $P_{M,N}$ arrayed two-dimensionally in M rows and N columns in the photodetecting unit 10 into regions each including pixels in Q rows and R columns. Each unit region includes QR pixels. The binning region is obtained by dividing the unit regions arrayed two-dimensionally in (M/Q) rows and (N/R) columns into regions each including unit regions in K rows and one column. Each binning region includes K unit regions, and includes KQR pixels. Here, Q, R, and K are each an integer of 1 or more. FIG. 3 illustrates a case in which Q=R=K=2. The solid-state imaging device of the embodiment has a characteristic when K is 2 or more.

M is preferably an integer multiple of KQ, and N is preferably an integer multiple of R. However, even when M is not an integer multiple of KQ or N is not an integer multiple of R, the unit region and the binning region may be set as described above, and for remaining pixels not included in any binning region, output values of the pixels may not be used for digital value output of the output unit 20.

The control unit 30 closes the readout switches $SW_1$ of the pixels included in the binning regions in the row for each row sequentially for the binning regions arrayed two-dimensionally in (M/KQ) rows and (N/R) columns in the photodetecting unit 10, inputs the charges generated in the photodiodes PD of the pixels to the output unit 20, and repeatedly outputs the digital value according to the sum of amounts of the charges output from the KQR pixels included in each binning region K times in a column order from the output unit 20. Periods in which the readout switches $SW_1$ of the pixels included in the binning region in each row are closed may exactly match, may partially overlap, or may not overlap at all.

When Q=R=K=1, the binning region and the unit region match each other, one pixel is included in each unit region, and the output unit 20 outputs a digital value according to the amount of charge output from each pixel $P_{m,n}$. When K=1, the binning region and the unit region match each other, and the output unit 20 outputs a digital value according to the sum of amounts of charges output from the QR pixels included in each unit region once. When K≥2, K unit regions are included in each binning region, and the output unit 20 repeatedly outputs a digital value according to the sum of amounts of charges output from KQR pixels included in each binning region K times.

The output unit 20 includes the storage unit 24 which stores the digital value according to the sum of amounts of the charges output from KQR pixels included in each binning region. Further, the control unit 30 repeatedly reads and outputs the digital values stored in the storage unit 24 K times in a column order from the storage unit. Any memory may be used as the storage unit 24. As the storage unit 24, a FIFO (First In First Out) memory may be used.

Next, a configuration example and an operation example of the output unit 20 of the solid-state imaging device 1 will be described with reference to FIG. 4 to FIG. 9. Here, it is assumed that the photodetecting unit 10 and the output unit 20 illustrated in FIG. 1 form one block, and a plurality of blocks 1 to B are arranged in parallel. The integration circuit and the hold circuit form a signal readout unit, and a FIFO memory is used as the storage unit. Further, Q=R=1.

Figure 4:
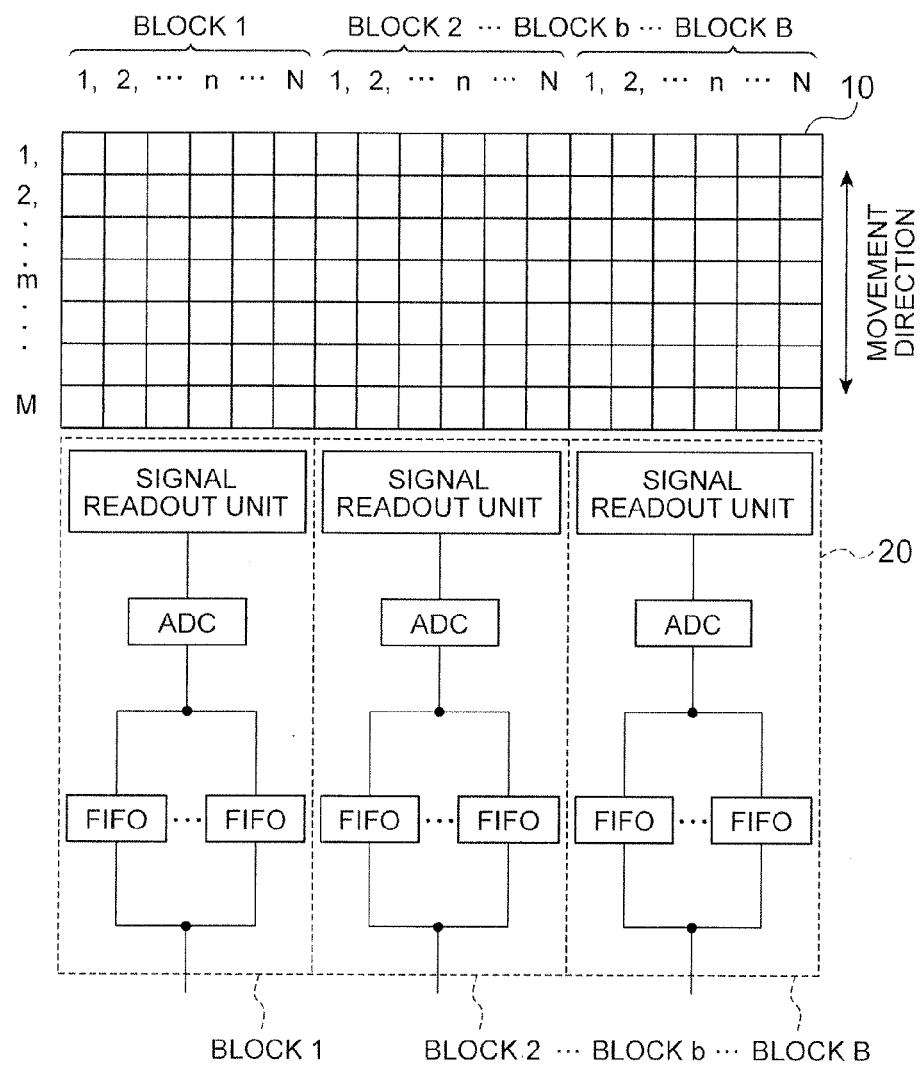
FIG. 4 is a diagram illustrating a first configuration example of an output unit 20 of the solid-state imaging device 1.
Figure 5:
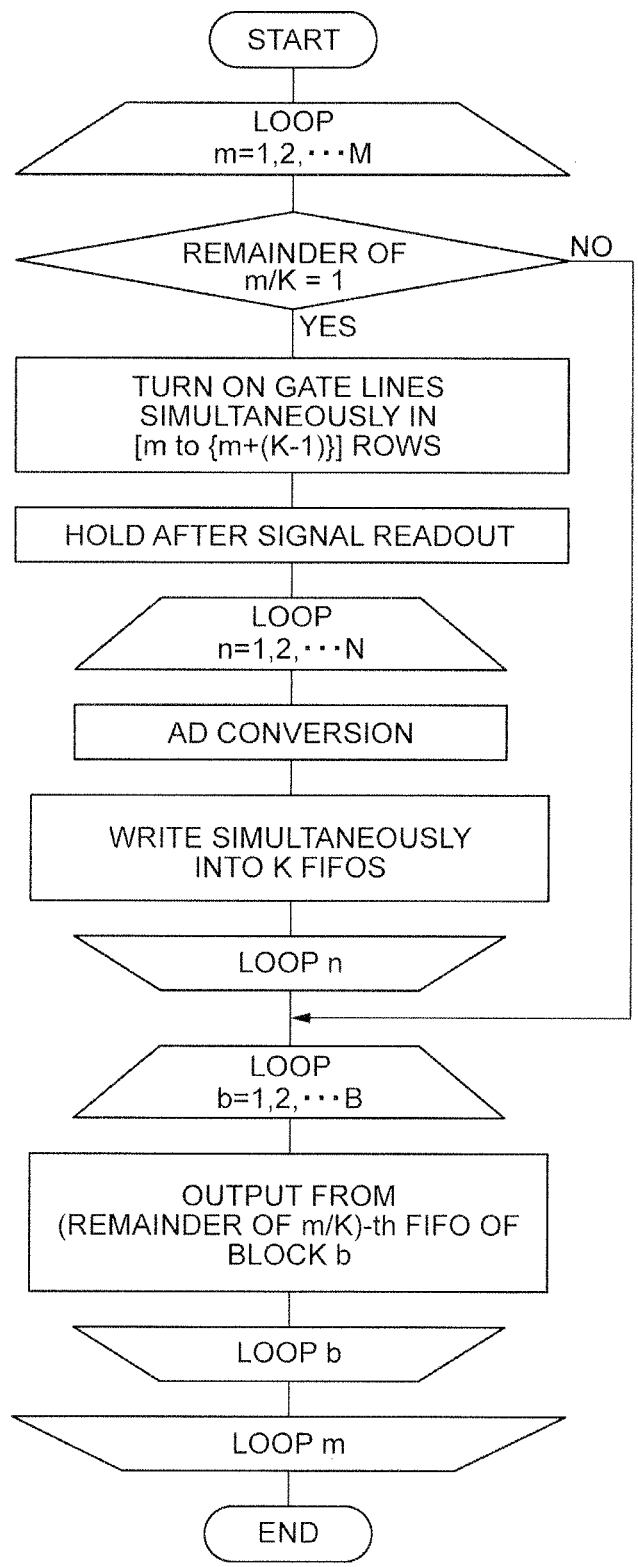
FIG. 5 is a flowchart illustrating an operation example in the first configuration example of the output unit 20 of the solid-state imaging device 1.
Figure 6:
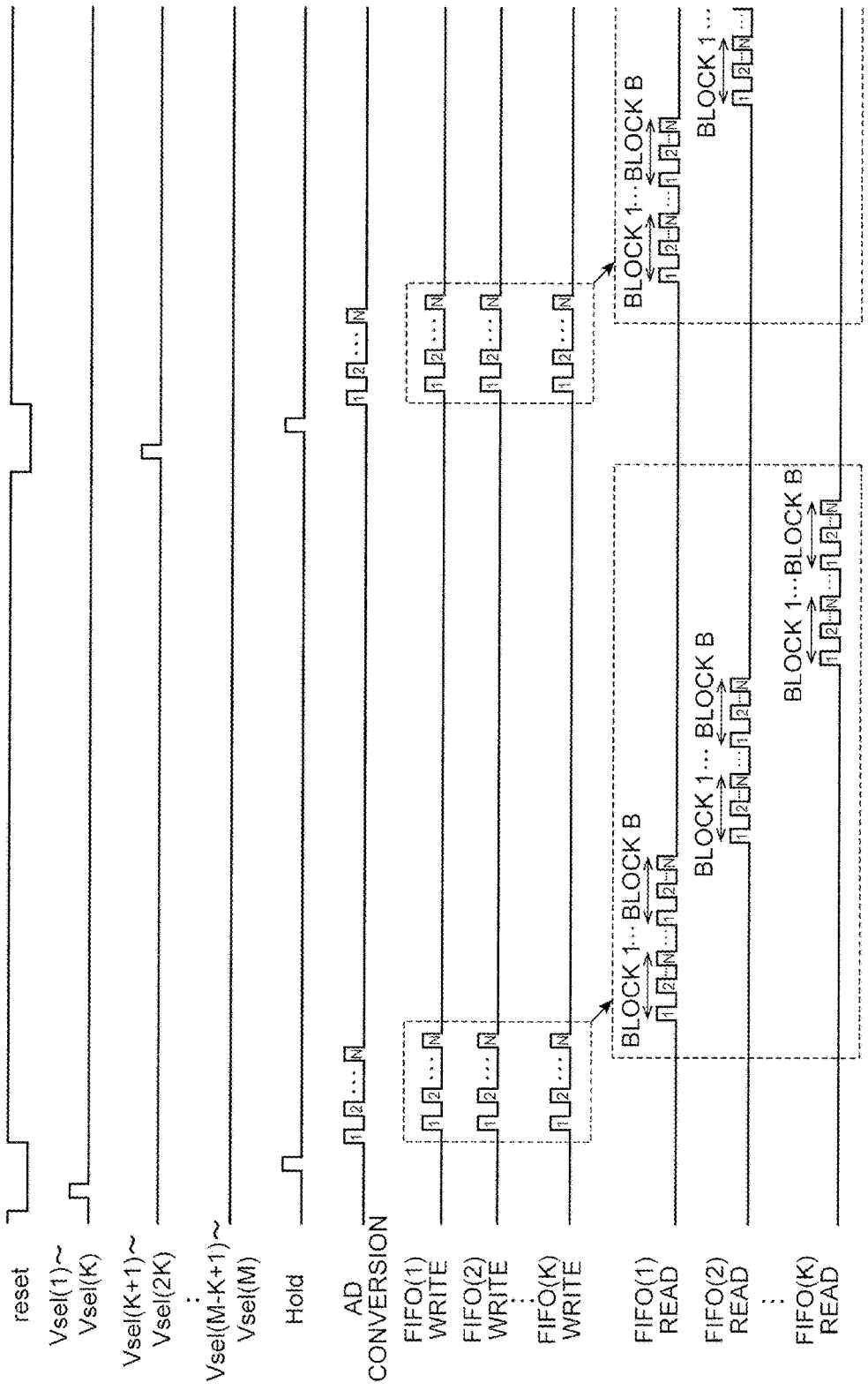
FIG. 6 is a timing chart illustrating the operation example in the first configuration example of the output unit 20 of the solid-state imaging device 1.

FIG. 4 is a diagram illustrating a first configuration example of the output unit 20 of the solid-state imaging device 1. FIG. 5 is a flowchart illustrating an operation example in the first configuration example of the output unit 20 of the solid-state imaging device 1. FIG. 6 is a timing chart illustrating the operation example in the first configuration example of the output unit 20 of the solid-state imaging device 1.

In the first configuration example illustrated in FIG. 4, the output unit 20 includes, as the storage unit, K FIFO memories that store the digital value according to the sum of amounts of the charges output from K pixels included in each binning region in a column order. The K FIFO memories are provided in parallel and have a common input terminal and a common output terminal. The control unit 30 sequentially outputs the digital values from the K FIFO memories so that the digital value according to the sum of amounts of the charges output from the K pixels included in each binning region is repeatedly output K times in a column order.

As in the flowchart illustrated in FIG. 5 and the timing chart illustrated in FIG. 6, in a period in which the reset control signal Reset is at a low level, K signals of the first row selection control signal Vsel(1) to the K-th row selection control signal Vsel(K) are brought to a high level in the same period, and then, the hold control signal Hold is changed from a high level to a low level, thus, a voltage value according to the amount of charge output from each of K pixels $P_{1,n}$ to $P_{K,n}$ included in each binning region is output from the integration circuit $21_n$ and is held by the hold circuit $22_n$. The voltage values held by the hold circuits $22_1$ to $22_N$ are input to the AD conversion unit 23 in a column order and subjected to AD conversion. The digital values output in a column order from the AD conversion unit 23 are simultaneously written into the K FIFO memories. This operation is performed in parallel in the blocks 1 to B.

The digital values are read in a column order from the first FIFO memory in an order of blocks 1 to B. That is, the digital values are read in a column order from the first FIFO memory in block 1, the digital values are read in a column order from the first FIFO memory in block 2, the digital values are similarly read for the subsequent blocks, and lastly, the digital values are read in a column order from the first FIFO memory in block B. Subsequently, the digital values are read in a column order from the second FIFO memory in an order of blocks 1 to B. Lastly, the digital values are similarly read in a column order from the K-th FIFO memory in an order of blocks 1 to B.

When the reading of the binning regions in the first row (reading of the pixels in the first row to the K-th row) ends in this way, reading of the binning regions in the second row (reading of the pixels in the (K+1)-th row to the (2K)-th row) is similarly performed, and lastly, reading of the binning regions in the (M/K)-th row (reading of the pixels in the (M−K+1)-th row to the M-th row) is performed. By doing so, it is possible to repeatedly output the digital value according to the sum of amounts of the charges output from the K pixels included in each binning region K times and obtain the image data for one frame.

Figure 7:
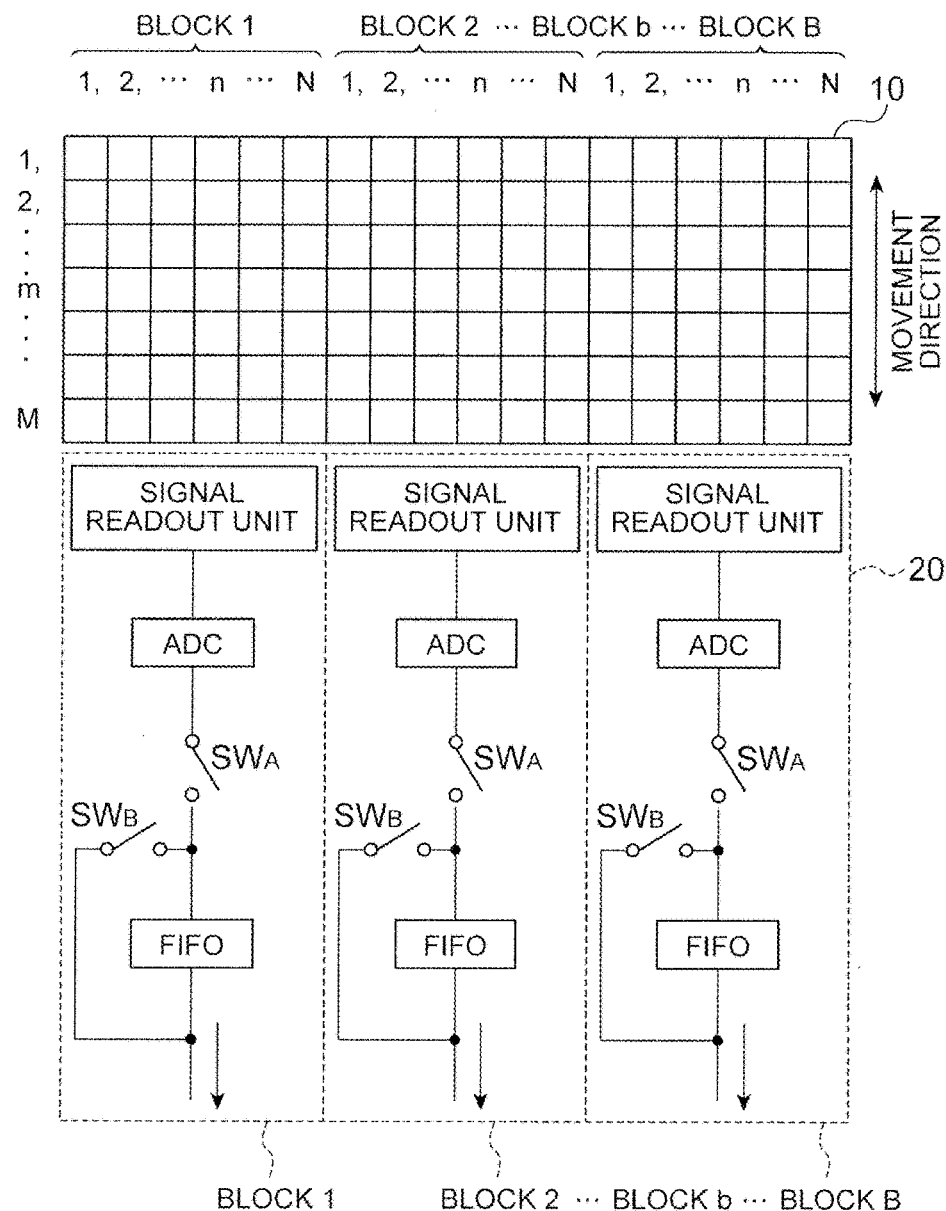
FIG. 7 is a diagram illustrating a second configuration example of the output unit 20 of the solid-state imaging device 1.
Figure 8:
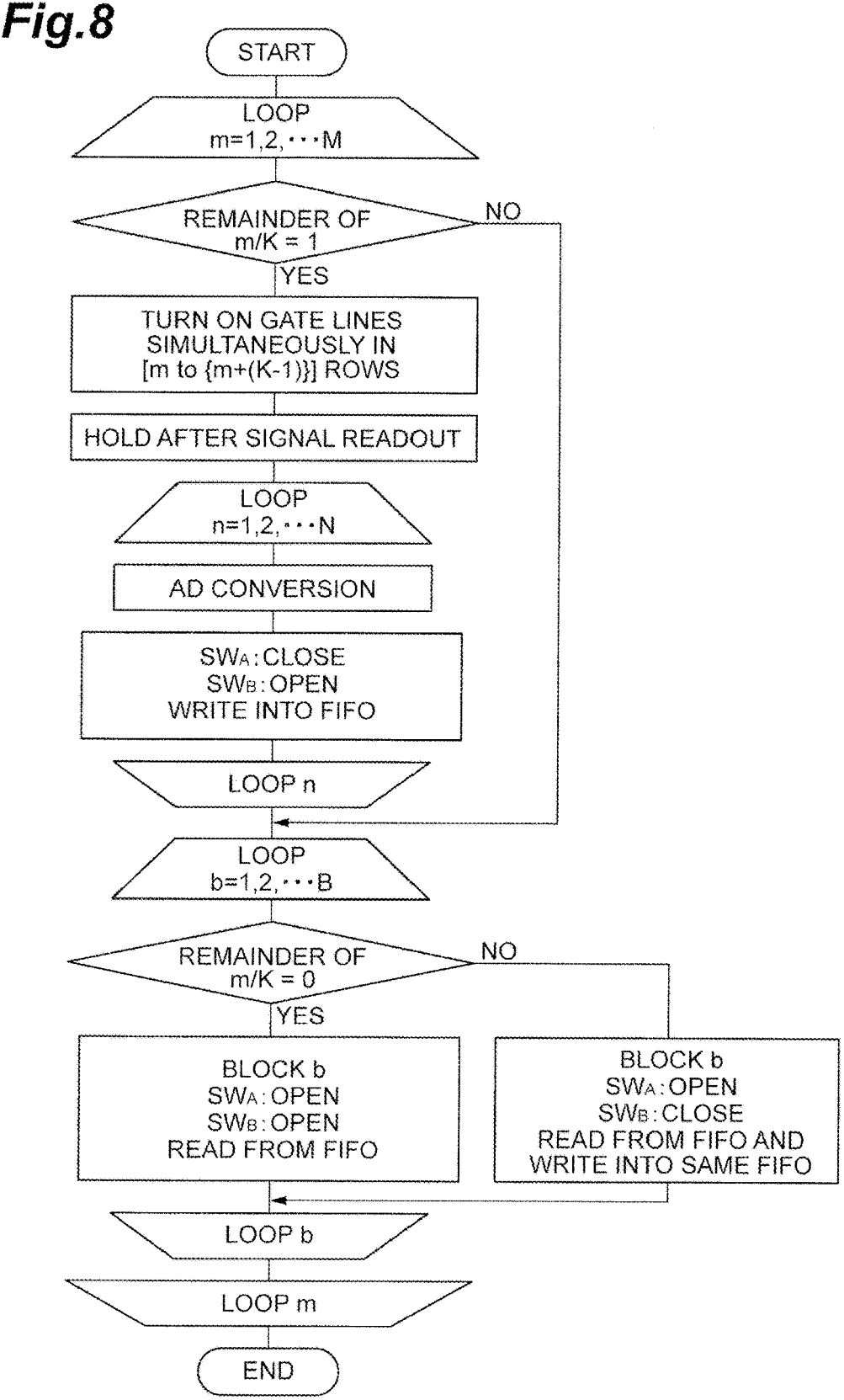
FIG. 8 is a flowchart illustrating an operation example in the second configuration example of the output unit 20 of the solid-state imaging device 1.
Figure 9:
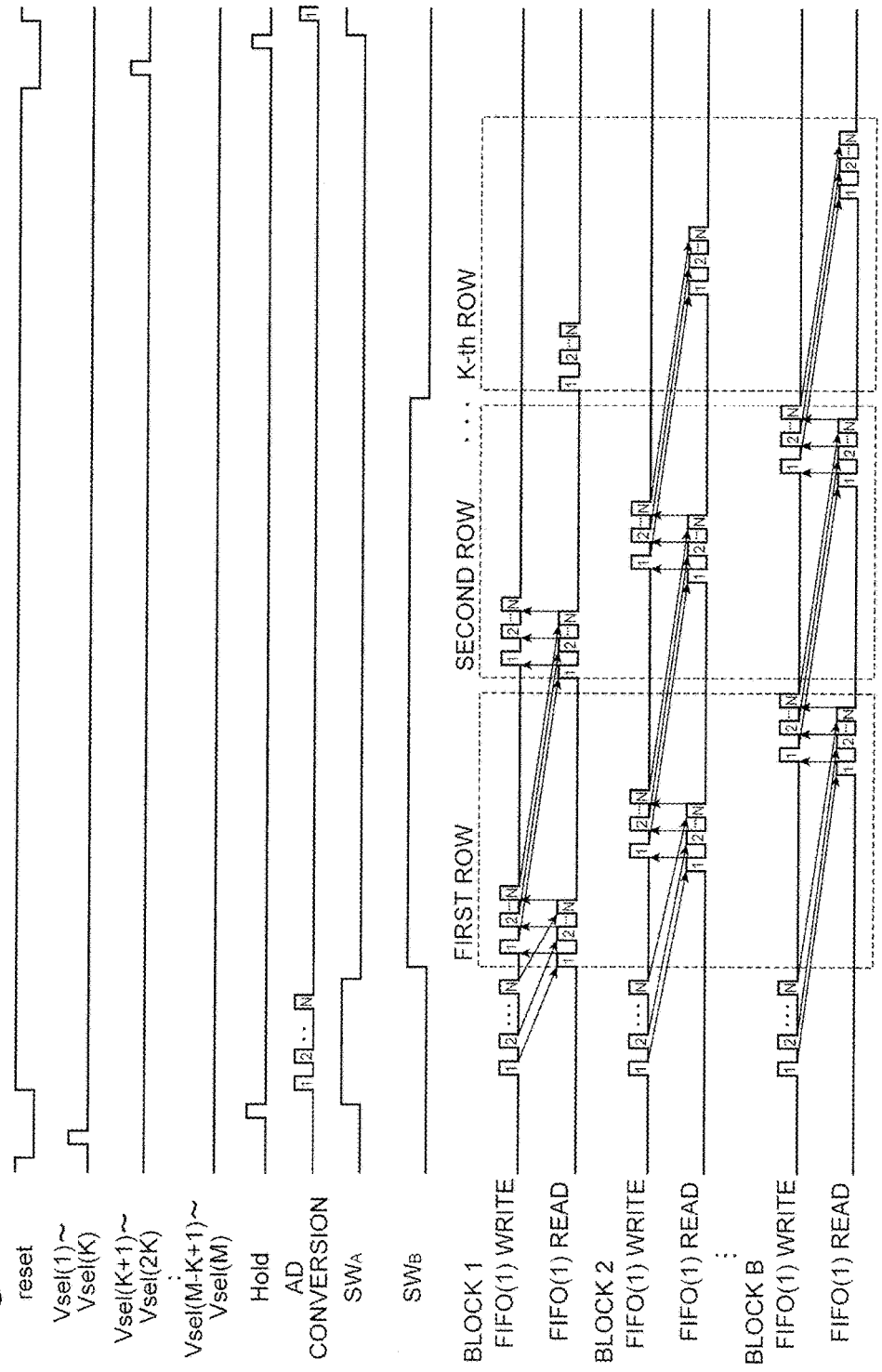
FIG. 9 is a timing chart illustrating the operation example in the second configuration example of the output unit 20 of the solid-state imaging device 1.

FIG. 7 is a diagram illustrating a second configuration example of the output unit 20 of the solid-state imaging device 1. FIG. 8 is a flowchart illustrating an operation example in the second configuration example of the output unit 20 of the solid-state imaging device 1. FIG. 9 is a timing chart illustrating the operation example in the second configuration example of the output unit 20 of the solid-state imaging device 1.

In the second configuration example illustrated in FIG. 7, the output unit 20 includes, as the storage unit, one FIFO memory that stores the digital value according to the sum of amounts of the charges output from K pixels included in each binning region in a column order. A switch $SW_A$ is provided between an input terminal of the FIFO memory and an output terminal of the AD conversion unit, and a switch $SW_B$ is provided between the input terminal and an output terminal of the FIFO memory. The control unit 30 outputs the digital value from this FIFO memory and stores the digital value in the FIFO memory so that the digital value according to the sum of amounts of the charges output from the K pixels included in each binning region is repeatedly output K times in a column order.

As in the flowchart illustrated in FIG. 8 and the timing chart illustrated in FIG. 9, in a period in which the reset control signal Reset is at a low level, K signals of the first row selection control signal Vsel(1) to the K-th row selection control signal Vsel(K) are brought to a high level in the same period, and then, the hold control signal Hold is changed from a high level to a low level, thus, a voltage value according to the amount of charge output from each of K pixels $P_{1,n}$ to $P_{K,n}$ included in each binning region is output from the integration circuit $21_n$ and is held by the hold circuit $22_n$. The voltage values held by the hold circuits $22_1$ to $22_N$ are input to the AD conversion unit 23 in a column order and subjected to AD conversion. The digital values output in a column order from the AD conversion unit 23 are written into the FIFO memory via the switch $SW_A$. This operation is performed in parallel in the blocks 1 to B.

The switch $SW_A$ is opened, the switch $SW_B$ is closed, and the digital values are read once in a column order from the FIFO memory and written into the FIFO memory again in an order of blocks 1 to B. This is repeated K times. Here, in the K-th repetition, since it is not necessary to write the read digital values into the FIFO memory again, the switch $SW_B$ is opened.

When the reading of the binning regions in the first row (reading of the pixels in the first row to the K-th row) ends in this way, reading of the binning regions in the second row (reading of the pixels in the (K+1)-th row to the (2K)-th row) is similarly performed, and lastly, reading of the binning regions in the (M/K)-th row (reading of the pixels in the (M−K+1)-th row to the M-th row) is performed. By doing so, it is possible to repeatedly output the digital value according to the sum of amounts of the charges output from the K pixels included in each binning region K times and obtain the image data for one frame.

Figure 10:
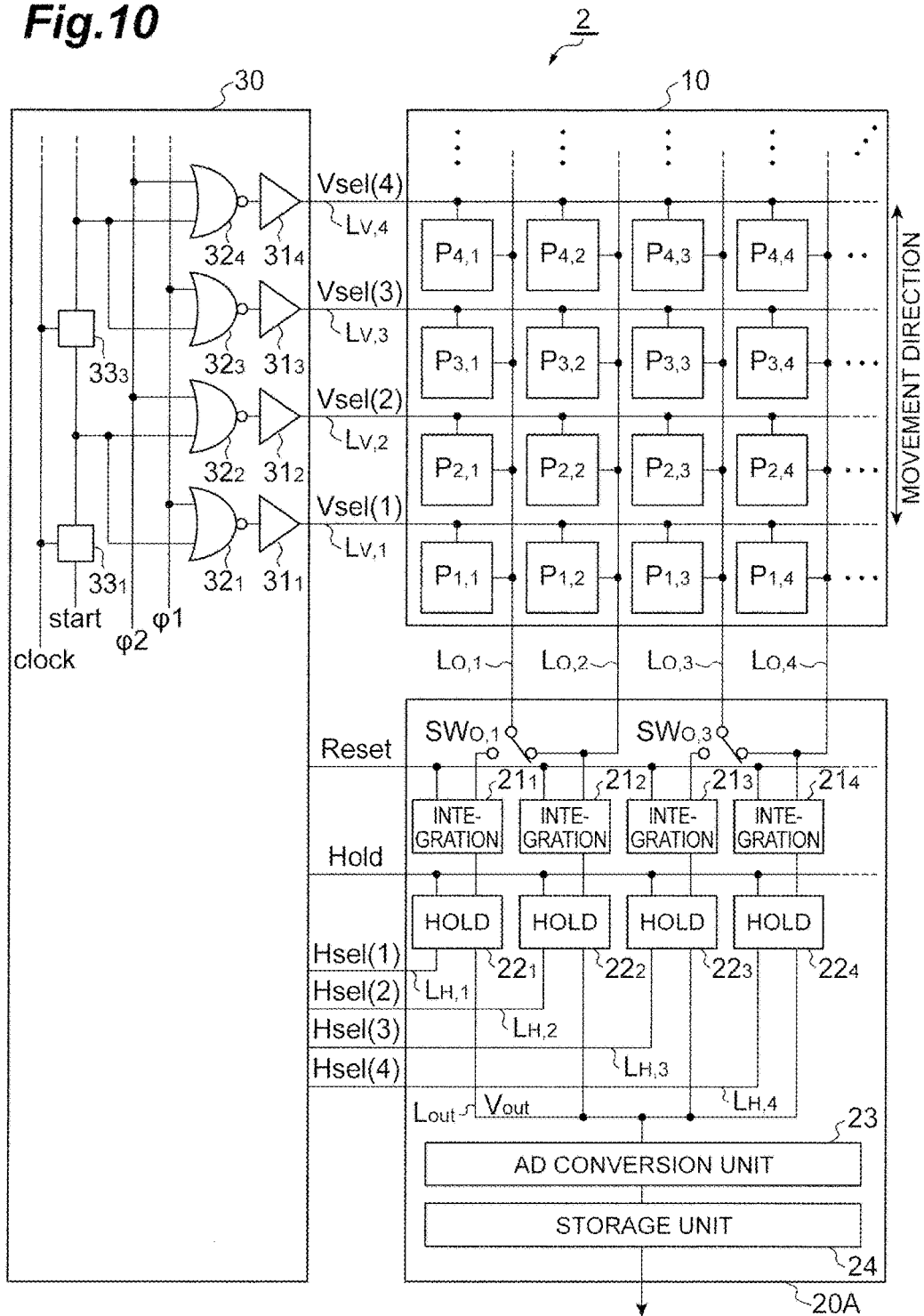
FIG. 10 is a diagram illustrating a configuration of a solid-state imaging device 2 of a second embodiment.

Next, a second embodiment will be described. FIG. 10 is a diagram illustrating a configuration of a solid-state imaging device 2 of the second embodiment. The solid-state imaging device 2 includes a photodetecting unit 10, an output unit 20A, and a control unit 30. The photodetecting unit 10 in the second embodiment has the same configuration as the photodetecting unit 10 in the first embodiment. The control unit 30 in the second embodiment has the same configuration as the control unit 30 in the first embodiment. Here, a specific configuration of the control unit 30 is illustrated in FIG. 10. Further, in FIG. 10, the first to fourth rows in the M rows are illustrated, and the first to fourth columns in the N columns are illustrated. The same applies to the other rows or the other columns.

A configuration of the output unit 20A in the second embodiment is different from the configuration of the output unit 20 in the first embodiment in that the output unit further includes binning changeover switches $SW_{O,1}$, $SW_{O,3}$, . . . . The binning changeover switch $SW_{O,1}$ selectively connects the first column readout line $L_{O,1}$ to the input terminal of any one of the integration circuit $21_1$ and the integration circuit $21_2$. At the time of binning, the first column readout line $L_{O,1}$ is connected to the input terminal of the integration circuit $21_2$ by the binning changeover switch $SW_{O,1}$, and the charges are input from both of the first column readout line $L_{O,1}$ and the second column readout line $L_{O,2}$ to the input terminal of the integration circuit $21_2$. Further, at the time of binning, only the integration circuit $21_2$ in the integration circuit $21_1$ and the integration circuit $21_2$ operates, and only the hold circuit $22_2$ in the hold circuit $22_1$ and the hold circuit $22_2$ operates. The same applies to the other columns in a combination of the (n−1)-th column of the odd-numbered column and the n-th column of the even-numbered column.

The control unit 30 includes buffer circuits $31_1$, $31_2$, $31_3$, $31_4$, ..., NOR gate circuits $32_1$, $32_2$, $32_3$, $32_4$, ..., and latch circuits $33_1$, $33_3$, .... The latch circuits $33_1$, $33_3$, ... are connected in series to constitute a shift register, and sequentially shift the value of the start signal to the subsequent stage in synchronization with a pulse rising edge of a clock signal with a certain period. The output value of the latch circuit $33_1$ is input to each of the latch circuit $33_3$ of the subsequent stage and the NOR gate circuits $32_1$ and $32_2$. The output value of the latch circuit $33_3$ is input to each of the latch circuit $33_5$ of the subsequent stage and the NOR gate circuits $32_3$ and $32_4$.

For the (m−1)-th row of the odd-numbered row, the NOR gate circuit $32_{m-1}$ receives the output value of the latch circuit $33_{m-1}$ and the $\phi1$ signal value, and outputs a signal value obtained by inverting a logical sum of the two input values. For the m-th row of the even-numbered row, the NOR gate circuit $32_m$ receives the output value of the latch circuit $33_{m-1}$ and the $\phi2$ signal value, and outputs a signal value obtained by inverting a logical sum of the two input values. Each buffer circuit $31_m$ outputs the output value of the NOR gate circuit $32_m$ as the m-th row selection control signal Vsel(m) to the m-th row selection line $L_{V,m}$.

Figure 11:
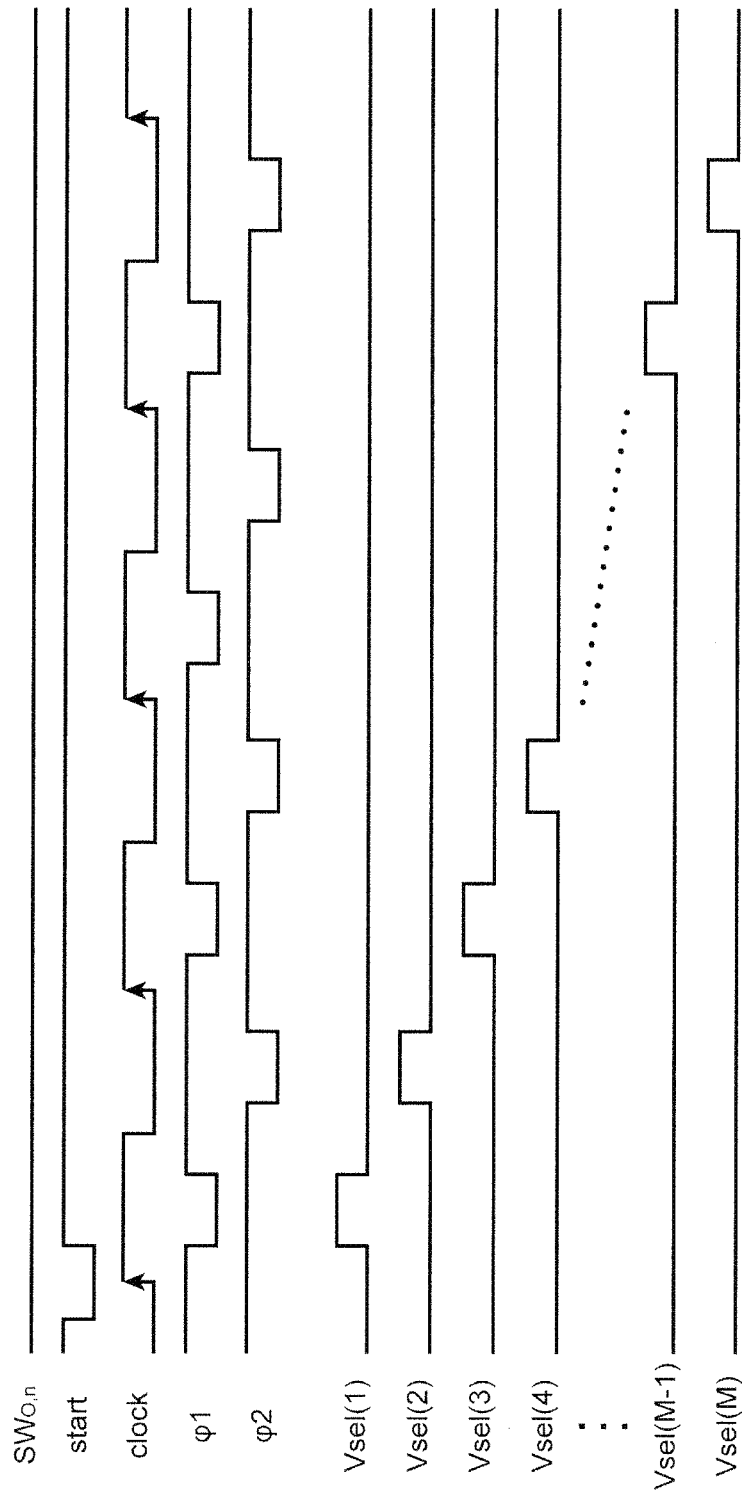
FIG. 11 is a timing chart illustrating a first operation example of the solid-state imaging device 2.

FIG. 11 is a timing chart illustrating a first operation example of the solid-state imaging device 2. In the first operation example, Q=R=K=1. In the first operation example, in the output unit 20A, the n-th column readout line $L_{O,n}$ is connected to the input terminal of the integration circuit $21_n$ in one-to-one correspondence by the binning changeover switches $SW_{O,1}$, $SW_{O,3}$, ....

In the first operation example, M row selection control signals Vsel(1) to Vsel(M) are sequentially brought to a high level one by one during a certain period of time. Only one pulse rising edge of the clock signal is present in a period in which the start signal is at a low level. The latch circuits $33_1$, $33_3$, ... shift a low level of the Start signal to a subsequent stage in synchronization with the pulse rising edge of the clock signal. The latch circuits $33_1$, $33_3$, ... hold the respective output values over a period from a rising edge of the clock signal to a next rising edge.

In a period in which an output of the latch circuit $33_1$ is at a low level, when a $\phi1$ signal is brought to a low level over a certain period of time, an output of the NOR gate circuit $32_1$ is brought to a high level over the certain period of time, and the first row selection control signal Vsel(1) is brought to a high level over the certain period of time. Subsequently, when $\phi2$ signal is brought to a low level over a certain period of time, an output of the NOR gate circuit $32_2$ is brought to a high level over the certain period of time, and the second row selection control signal Vsel(2) is brought to a high level over the certain period of time.

Thereafter, when the pulse of the clock signal rises once, an output of the latch circuit $33_3$ is brought to a low level. In this period, when the $\phi1$ signal is brought to a low level over a certain period of time, an output of the NOR gate circuit $32_3$ is brought to a high level over the certain period of time, and the third row selection control signal Vsel(3) is brought to a high level over the certain period of time. Subsequently, when the $\phi2$ signal is brought to a low level over a certain period of time, an output of the NOR gate circuit $32_4$ is brought to a high level over the certain period of time, and the fourth row selection control signal Vsel(4) is brought to a high level over the certain period of time. The same applies to subsequent rows.

Figure 12:
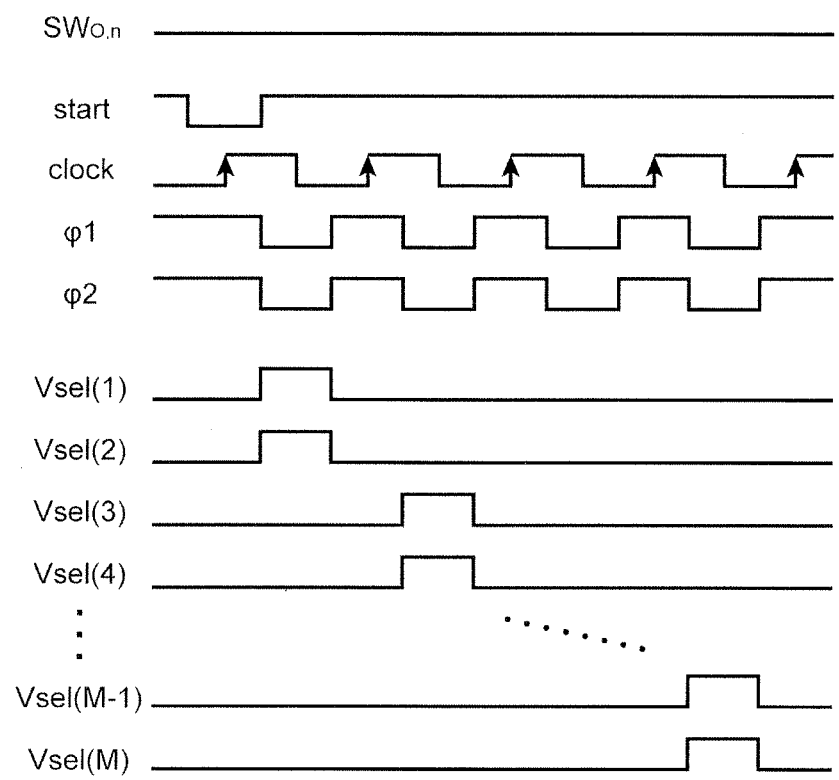
FIG. 12 is a timing chart illustrating a second operation example of the solid-state imaging device 2.

FIG. 12 is a timing chart illustrating a second operation example of the solid-state imaging device 2. In the second operation example, Q=R=2, and K=1. In the second operation example, in the output unit 20A, both of the (n−1)-th column readout line $L_{O,n-1}$ of the odd-numbered column and the n-th column readout line $L_{O,n}$ of the even-numbered column are connected to the input terminal of the integration circuit $21_n$ of the even-numbered column by the binning changeover switches $SW_{O,1}$, $SW_{O,3}$, ....

In the second operation example, M row selection control signals Vsel(1) to Vsel(M) are sequentially brought to a high level two by two during a certain period of time. Only one pulse rising edge of the clock signal is present in a period in which the start signal is at a low level. The latch circuits $33_1$, $33_3$, ... shift a low level of the Start signal to a subsequent stage in synchronization with the pulse rising edge of the clock signal. The latch circuits $33_1$, $33_3$, ... hold the respective output values over a period from a rising edge of the clock signal to a next rising edge.

In a period in which an output of the latch circuit $33_1$ is at a low level, a $\phi1$ signal and a $\phi2$ signal are brought to a low level over a certain period of time at the same time. Thus, outputs of the NOR gate circuits $32_1$ and $32_2$ are brought to a high level over the certain period of time at the same time, and the first row selection control signal Vsel(1) and the second row selection control signal Vsel(2) are brought to a high level over the certain period of time at the same time.

Thereafter, when the pulse of the clock signal rises once, an output of the latch circuit $33_3$ is brought to a low level. In this period, the $\phi1$ signal and the $\phi2$ signal are brought to a low level over a certain period of time at the same time. Thus, outputs of the NOR gate circuits $32_3$ and $32_4$ are brought to a high level over the certain period of time at the same time, and the third row selection control signal Vsel(3) and the fourth row selection control signal Vsel(4) are brought to a high level over the certain period of time at the same time. The same applies to subsequent rows.

In a period from a time when the two row selection control signals Vsel(1) and Vsel(2) are changed from a high level to a low level to a time when the two row selection control signals Vsel(3) and Vsel(4) are changed from a low level to a high level, processes following the process of the hold circuit are performed.

In the second operation example, the output unit 20A outputs the digital value according to the sum of amounts of the charges output from KQR (=4) pixels included in each binning region K (=1) times.

Figure 13:
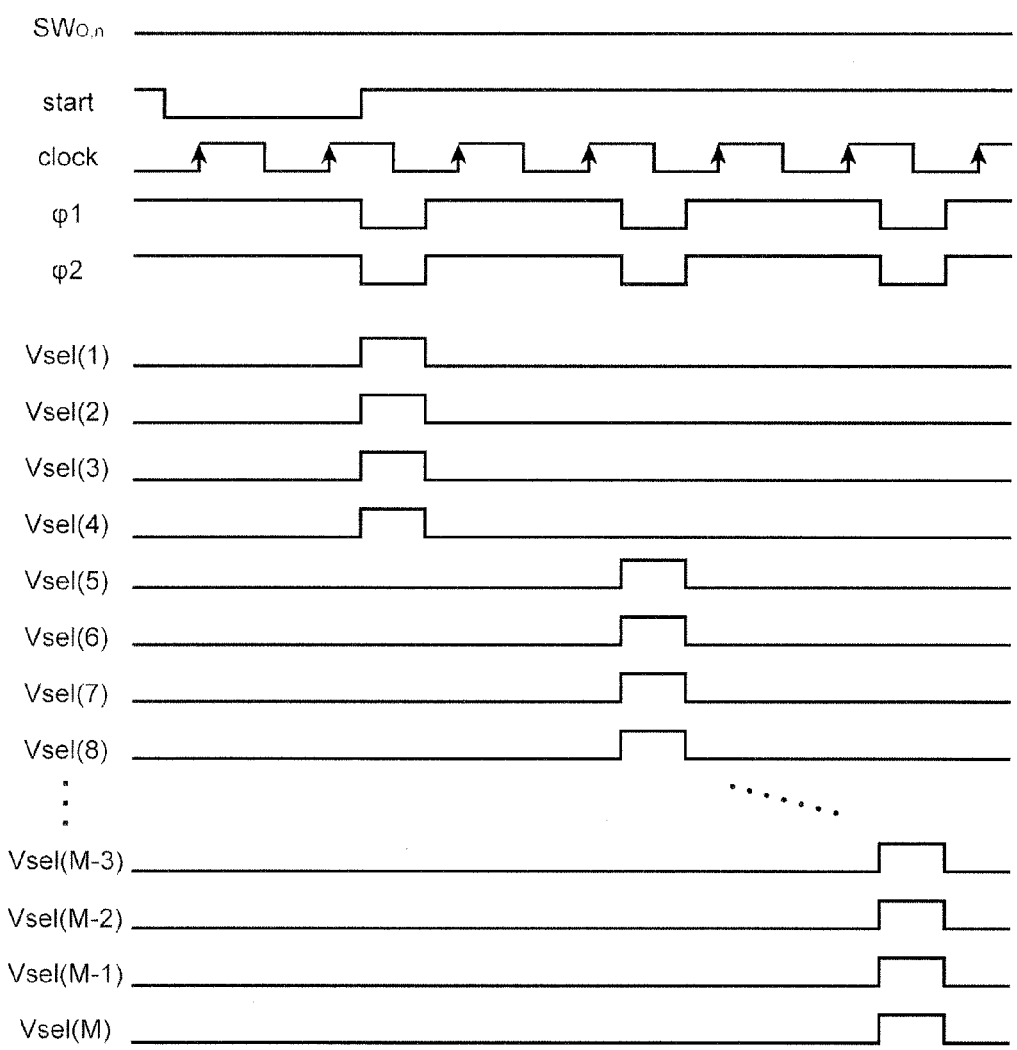
FIG. 13 is a timing chart illustrating a third operation example of the solid-state imaging device 2.

FIG. 13 is a timing chart illustrating a third operation example of the solid-state imaging device 2. In the third operation example, Q=R=K=2. In the third operation example, in the output unit 20A, both of the (n−1)-th column readout line $L_{O,n-1}$ of the odd-numbered column and the n-th column readout line $L_{O,n}$ of the even-numbered column are connected to the input terminal of the integration circuit $21_n$ of the even-numbered column by the binning changeover switches $SW_{O,1}$, $SW_{O,3}$, ....

In the third operation example, M row selection control signals Vsel(1) to Vsel(M) are sequentially brought to a high level four by four during a certain period of time. Two pulse rising edges of the clock signal are present in a period in which the start signal is at a low level. The latch circuits $33_1$, $33_3$, ... shift the low level of the Start signal to a subsequent stage in synchronization with the pulse rising edge of the clock signal. The latch circuits $33_1$, $33_3$, ... hold the respective output values over a period from a rising edge of the clock signal to a next rising edge.

In a period in which outputs of the latch circuits $33_1$ and $33_3$ are at a low level, the φ1 signal and the φ2 signal are brought to a low level over a certain period of time at the same time. Thus, outputs of the NOR gate circuits $32_1$ to $32_4$ are brought to a high level over the certain period of time at the same time, and the four row selection control signals Vsel(1) to Vsel(4) are brought to a high level over the certain period of time at the same time.

Thereafter, when the pulse of the clock signal rises twice, outputs of the latch circuits $33_5$ and $33_7$ are brought to a low level. In this period, the φ1 signal and the φ2 signal are brought to a low level over a certain period of time at the same time. Thus, outputs of the NOR gate circuits $32_5$ to $32_8$ are brought to a high level over the certain period of time at the same time, and the four row selection control signals Vsel(5) to Vsel(8) are brought to a high level over the certain period of time at the same time. The same applies to subsequent rows.

In a period from a time when the four row selection control signals Vsel(1) to Vsel(4) are changed from a high level to a low level to a time when the four row selection control signals Vsel(5) to Vsel(8) are changed from a low level to a high level, processes following the process of the hold circuit are performed.

In the third operation example, the output unit 20A repeatedly outputs the digital value according to the sum of amounts of the charges output from KQR (=8) pixels included in each binning region K (=2) times.

Figure 14:
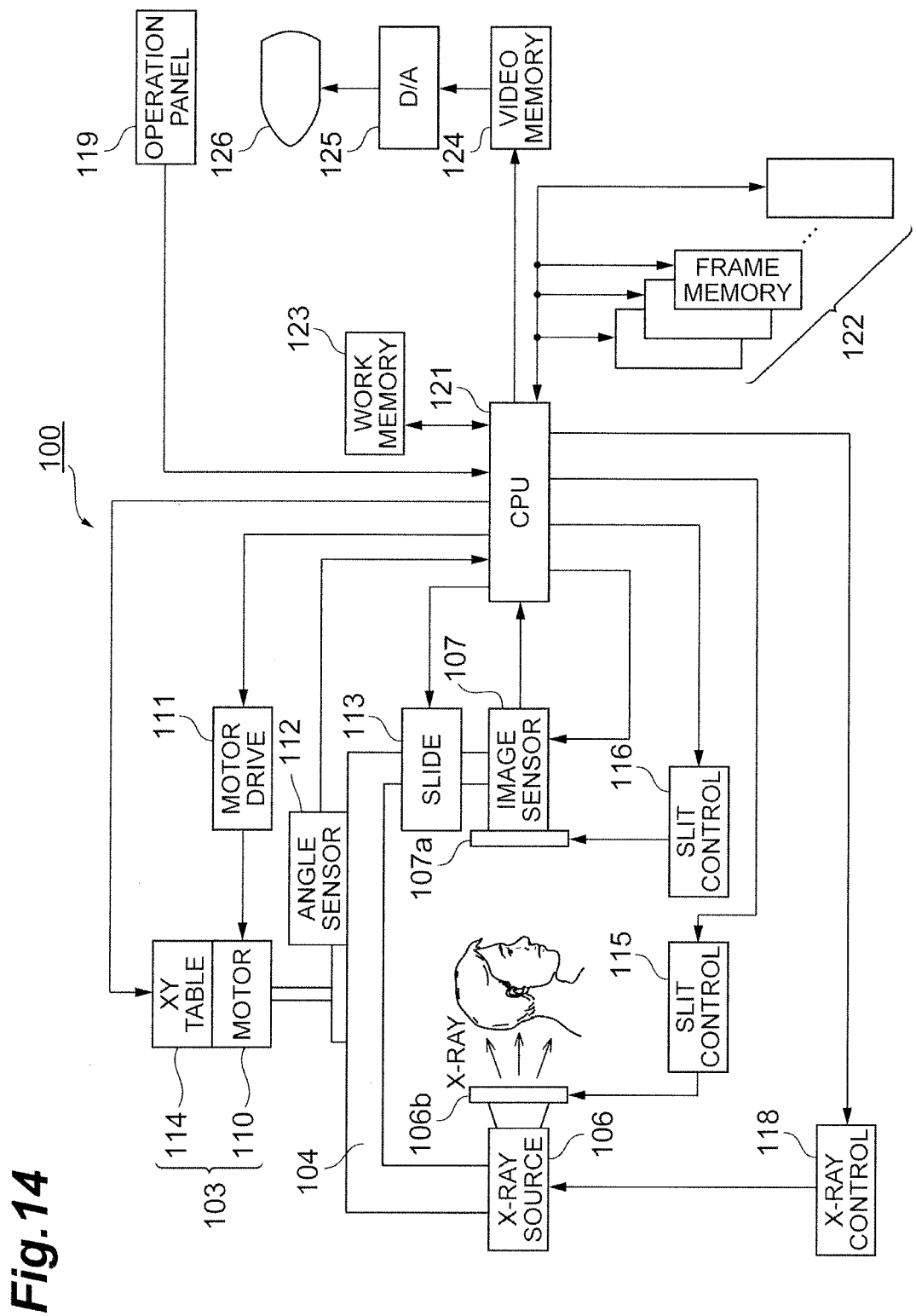
FIG. 14 is a diagram illustrating a configuration of an X-ray imaging system 100 of the embodiment.

Next, an embodiment of an X-ray imaging system including the solid-state imaging device of the embodiment will be described. FIG. 14 is a diagram illustrating a configuration of an X-ray imaging system 100 of this embodiment. The X-ray imaging system 100 of this embodiment includes a solid-state imaging device and an X-ray generating device, and X-rays output from the X-ray generating device and transmitted through an imaging object can be imaged by the solid-state imaging device and used for inspection of the imaging object.

In the X-ray imaging system 100 illustrated in FIG. 14, the X-ray generating device 106 generates X-rays toward a subject (imaging object). An irradiation field of the X-rays generated from the X-ray generating device 106 is controlled by a first slit plate 106b. The X-ray generating device 106 includes an X-ray tube built thereinto, and the amount of X-ray irradiation to the subject is controlled by adjusting conditions such as a tube voltage, a tube current, and an energization time of the X-ray tube. The X-ray imager 107 includes a CMOS solid-state imaging device having a plurality of two-dimensionally arrayed pixels built thereinto, and images an X-ray image passing through the subject. A second slit plate 107a that limits an X-ray incidence region is provided in front of the X-ray imager 107.

A rotation arm 104 holds the X-ray generating device 106 and the X-ray imager 107 so that the X-ray generating device faces the X-ray imager, and rotates the X-ray generating device and the X-ray imager around the subject at the time of panoramic tomography. Further, a slide mechanism 113 for linearly displacing the X-ray imager 107 with respect to the subject at the time of linear tomography is provided. The rotation arm 104 is driven by an arm motor 110 constituting a rotary table, and a rotation angle thereof is detected by an angle sensor 112. Further, the arm motor 110 is mounted on a movable portion of an XY table 114, and a rotation center thereof is arbitrarily adjusted in a horizontal plane.

An image signal output from the X-ray imager 107 is loaded into a CPU (central processing unit) 121 and then stored in a frame memory 122. A tomographic image along any tomographic plane is reproduced from image data stored in the frame memory 122 through a predetermined arithmetic process. The reproduced tomographic image is output to a video memory 124, converted into an analog signal by a DA converter 125, displayed on an image display unit 126 such as a CRT (cathode ray tube), and is provided for various diagnoses.

A work memory 123 required for signal processing is connected to the CPU 121, and further, an operation panel 119 including a panel switch, an X-ray irradiation switch, and the like is also connected. Further, the CPU 121 is connected to each of a motor drive circuit 111 that drives the arm motor 110, slit control circuits 115 and 116 that control opening ranges of the first slit plate 106b and the second slit plate 107a, and an X-ray control circuit 118 that controls the X-ray generating device 106, and further, outputs a signal for driving the X-ray imager 107.

The X-ray control circuit 118 can perform feedback control on the amount of X-ray irradiation to the subject on the basis of a signal captured by the X-ray imager 107.

In the X-ray imaging system 100 configured as above, the solid-state imaging device 1 or 2 of the embodiment may be used as the X-ray imager 107. Further, in the X-ray imaging system 100, the solid-state imaging device of the embodiment moves in the column direction (a vertical direction in FIGS. 1, 3, 4, 7, and 10) in the photodetecting unit during an imaging period of time, that is, a direction in which K unit regions are arrayed in each binning region when K≥2. It is possible to reduce degradation of quality of an image obtained through a reconstruction process by performing a binning process on the unit regions in the movement direction.

Thus, in this embodiment, it is possible to obtain the output value according to the amount of incident light in each binning region that is long in a movement direction (column direction) from the solid-state imaging device, and to achieve improvement of an S/N ratio. Further, in this embodiment, it is possible to flexibly set a shape or a size of the binning region in units of pixels. In particular, a length in the column direction of the binning region can be appropriately set according to movement speed of the solid-state imaging device.

When the movement speed of the solid-state imaging device is v and the frame rate is f, the movement distance of the solid-state imaging device during one frame imaging period is v/f. Further, when a pixel pitch is d, the length in the column direction of each binning region is KQd. When the movement distance v/f during one frame imaging period is greater than the length KQd in the column direction of each binning region, that is, if v/f>KQd, degradation of quality of the image obtained through a reconstruction process is small. It is preferable for the K value and the Q value to be set to satisfy the condition.

In this embodiment, when each binning region in the photodetecting unit includes K unit regions, the output unit repeatedly outputs the digital value according to the sum of amounts of the charges output from the pixels included in each binning region K times in a column order. That is, the number of data of the output signals per frame is equal to the number (MN/QR) of the unit regions in the photodetecting unit regardless of the K value. Therefore, even when binning is performed as K≥2, it is not necessary for the processing of the output signals to be changed according to the K value, and it is easy to handle the output signals. Further, in this embodiment, even when the binning is performed as K≥2, the frame rate can be constant regardless of the K value.

When K≥2, it is possible to increase the frame rate, compared to the case where K=1.

In the solid-state imaging device of the embodiment, since it is not necessary for the processing of the output signals to be changed according to the K value even when binning is performed as K≥2, the device can be easily applied to an existing X-ray imaging system. When the solid-state imaging device of the embodiment is applied to an existing X-ray imaging system, it is not necessary to change the system (or only improve a partial peripheral portion of the solid-state imaging device), and it is possible to improve an S/N ratio without changing a reconstruction process and the like based on the output signals of the solid-state imaging device at all.

In the embodiment, the output unit repeatedly outputs the digital value rather than an analog value K times. Thus, it is possible to realize low power consumption of the solid-state imaging device.

Further, in the embodiment, since the storage unit 24 at a subsequent stage of the AD conversion unit 23 repeatedly outputs the digital value K times, there is a time margin in processes of each integration circuit $21_n$ and each hold circuit $22_n$ at a preceding stage of the AD conversion unit 23. Therefore, a period of time in which the input switch $SW_{31}$ of each hold circuit $22_n$ is open (that is, a period of time in which the hold control signal Hold is at a high level) can be made longer than usual, and a low-pass filter can be inserted between the output terminal of the integration circuit $21_n$ and the input terminal of the hold circuit $22_n$ to reduce noise. Although a time constant increases when the low-pass filter is inserted and transfer to the hold circuit $22_n$ becomes slow, there is no problem since there is a time margin.

Further, as a method of causing a time margin, processes (reading from a pixel, and processes of each integration circuit and each hold circuit) at a preceding stage of the AD conversion unit can be performed in a period in which reading from a FIFO is performed. In this case, sufficient time can be secured for reading from a pixel, sample and hold of each hold circuit, and the like, and a frame rate can be increased.

Although the anode terminal of the photodiode of each pixel is grounded and the cathode terminal of the photodiode is connected to the readout line via the readout switch in the above embodiment, the cathode terminal of the photodiode may be grounded and the anode terminal of the photodiode may be connected to the readout line via the readout switch. Although the switch is closed when the control signal for controlling the opening and closing operation of each switch is at a high level in the above embodiment, the switch may be closed when the control signal is at a low level.

In the above embodiment, binning in the column direction is performed by the binning changeover switch provided at a preceding stage of the integration circuit, but it is not limited thereto. An amplifier may be provided at a preceding stage of the AD conversion unit, the output switches $SW_{32}$ of the plurality of hold circuits may be simultaneously closed, and voltage values held by the plurality of hold circuits may be input to the amplifier to perform binning in the column direction. Further, digital values in a plurality of columns output from the AD conversion unit may be added to perform the binning in the column direction. The digital value according to the sum of amounts of the charges output from KQR pixels included in each binning region may be a digital value according to an average amount of charge per pixel obtained by dividing the sum of the charge amounts by KQR. In any case, the digital value is a value proportional to the sum of the charge amounts.

In the above embodiment, when M is not an integer multiple of KQ or N is not an integer multiple of R, the output values of the pixels may not be used for digital value output of the output unit 20 for remaining pixels not included in any binning region, but it is not limited thereto. The remaining pixels not included in any of binning regions each including the KQR pixels may be separated in every Q rows or every R columns and divided into binning regions (hereinafter referred to as "dummy binning regions") including L pixels less than KQR. In this case, a digital value that is a (KQR/L) multiple of a digital value output from the AD conversion unit according to the sum of amounts of the charges output from L pixels included in each dummy binning region may be output from the output unit 20 repeatedly K times.

In the above embodiment, the digital values are output in a column order from the output unit, but it is not limited thereto. The digital values may be output sequentially for each column from the output unit. For example, the digital values of the odd-numbered columns may be output in a column order from the output unit, and then, the digital values of the even-numbered columns may be output in a column order.

The solid-state imaging device, the X-ray imaging system, and the solid-state imaging device driving method according to the present invention are not limited to the embodiments and the configuration examples described above, and various modifications can be made.

The solid-state imaging device according to the above embodiment includes (1) a photodetecting unit in which MN pixels $P_{1,1}$ to $P_{M,N}$, each including a photodiode generating a charge of an amount according to an incident light intensity and a readout switch connected to the photodiode, axe arrayed two-dimensionally in M rows and N columns, (2) a row selection line $L_{V,m}$ applying an m-th row selection control signal for instructing an opening and closing operation to the readout switch of each of N pixels $P_{3,1}$ to $P_{m,N}$ in an m-th row in the photodetecting unit, (3) a readout line $L_{O,n}$ being connected to the readout switch of each of M pixels $P_{1,n}$ to $P_{M,n}$ in an n-th column in the photodetecting unit, and reading the charge generated in the photodiode of any of the M pixels $P_{1,n}$ to $P_{M,n}$ via the readout switch of the pixel, (4) an output unit being connected to each of the readout lines $L_{O,1}$ to $L_{O,N}$ and outputting a digital value generated on the basis of the amount of the charge input via the readout line $L_{O,n}$, and (5) a control unit controlling an opening and closing operation of the readout switch of each of MN pixels $P_{1,1}$ to $P_{M,N}$ in the photodetecting unit via the row selection lines $L_{V,1}$ to $L_{V,M}$ and controlling a digital value output operation in the output unit.

Further, in the solid-state imaging device described above, the control unit divides the pixels $P_{1,1}$ to $P_{M,N}$ arrayed two-dimensionally in M rows and N columns in the photodetecting unit into unit regions each including pixels of Q rows and R columns, divides the unit regions arrayed two-dimensionally in (M/Q) rows and (N/R) columns into binning regions each including unit regions of K rows and one column, closes the readout switches of the pixels included in the binning region in the row for each row sequentially for the binning regions arrayed two-dimensionally in (M/KQ) rows and (N/R) columns in the photodetecting unit, inputs the charges generated in the photodiodes of the pixels to the output unit, and repeatedly outputs the digital value according to the sum of amounts of the charges output from the KQR pixels included in each binning region from the output unit K times sequentially for each column. Here, M and N are each an integer of 2 or more, m is an integer of 1 or more and M or less, n is an integer of 1 or more and N or less, Q and R are each an integer of 1 or more, and K is an integer of 2 or more.

In the solid-state imaging device of the above configuration, the output unit may include a storage unit storing the digital value according to the sum of amounts of the charges output from the pixels included in each binning region, and the control unit may repeatedly read and output the digital value stored in the storage unit from the storage unit K times sequentially for each column.

In this case, the output unit may include, as the storage unit, K FIFO memories storing the digital value according to the sum of amounts of the charges output from the pixels included in each binning region sequentially for each column, and the control unit may cause the digital values to be sequentially output from the K FIFO memories so that the digital value according to the sum of amounts of the charges output from the pixels included in each binning region is repeatedly output K times sequentially for each column.

Alternatively, the output unit may include, as the storage unit, a FIFO memory storing the digital value according to the sum of amounts of the charges output from the pixels included in each binning region sequentially for each column, and the control unit may cause the digital value to be output from the FIFO memory and may cause the digital value to be stored in the FIFO memory so that the digital value according to the sum of amounts of the charges output from the pixels included in each binning region is repeatedly output K times sequentially for each column.

The solid-state imaging device of the above configuration may include a plurality of blocks each including the photodetecting unit and the output unit connected to each other by the readout line $L_{O,n}$, and the photodetecting units in the respective blocks may be arranged in parallel in the row direction.

The X-ray imaging system according to the above embodiment includes the solid-state imaging device of the above configuration, and an X-ray generating device, and X-rays output from the X-ray generating device and transmitted through an imaging object are imaged by the solid-state imaging device. Further, the X-ray imaging system may have a configuration in which the solid-state imaging device moves in the column direction in the photodetecting unit in the imaging period.

The solid-state imaging device driving method according to the above embodiment is a method for driving a solid-state imaging device including the photodetecting unit, the row selection line $L_{V,m}$, the readout line $L_{O,n}$, and the output unit of the above configuration, and the method includes dividing the pixels $P_{1,1}$ to $P_{M,N}$ arrayed two-dimensionally in M rows and N columns in the photodetecting unit into unit regions each including pixels of Q rows and R columns, dividing the unit regions arrayed two-dimensionally in (M/Q) rows and (N/R) columns into binning regions each including unit regions of K rows and one column, closing the readout switches of the pixels included in the binning region in the row for each row sequentially for the binning regions arrayed two-dimensionally in (M/KQ) rows and (N/R) columns in the photodetecting unit, inputting the charges generated in the photodiodes of the pixels to the output unit, and repeatedly outputting the digital value according to the sum of amounts of the charges output from the KQR pixels included in each binning region from the output unit K times sequentially for each column. Here, M and N are each an integer of 2 or more, m is an integer of 1 or more and M or less, n is an integer of 1 or more and N or less, Q and R are each an integer of 1 or more, and K is an integer of 2 or more.

In the solid-state imaging device driving method of the above configuration, in the output unit, a storage unit storing the digital value according to the sum of amounts of the charges output from the pixels included in each binning region may be used, and the digital value stored in the storage unit may be repeatedly read and output from the storage unit K times sequentially for each column.

In this case, in the output unit, as the storage unit, K FIFO memories storing the digital value according to the sum of amounts of the charges output from the pixels included in each binning region sequentially for each column may be used, and the digital values may be sequentially output from the K FIFO memories so that the digital value according to the sum of amounts of the charges output from the pixels included in each binning region is repeatedly output K times sequentially for each column.

Alternatively, in the output unit, as the storage unit, a FIFO memory storing the digital value according to the sum of amounts of the charges output from the pixels included in each binning region sequentially for each column may be used, and the digital value may be output from the FIFO memory and the digital value may be stored in the FIFO memory so that the digital value according to the sum of amounts of the charges output from the pixels included in each binning region is repeatedly output K times sequentially for each column.

INDUSTRIAL APPLICABILITY

The present invention can be used as a solid-state imaging device capable of outputting a signal that is easy to handle even when binning is performed, an X-ray imaging system including such a solid-state imaging device, and a method of driving a solid-state imaging device so that a signal that is easy to handle can be output even when binning is performed.

REFERENCE SIGNS LIST 1, 2—solid-state imaging device, 10—photodetecting unit, 20, 20A—output unit, $21_1$-$21_N$—integration circuit, $22_1$-$22_N$—hold circuit, 23—AD conversion unit, 24—storage unit, 30—control unit, $31_1$-$31_M$—buffer circuit, $32_1$-$32_M$—NOR gate circuit, $33_1$, $33_3$—latch circuit.

The invention claimed is:

1. A solid-state imaging device comprising:
a photodetecting unit including MN pixels $P_{1,1}$ to $P_{M,N}$, each including a photodiode generating a charge of an amount according to an incident light intensity and a readout switch connected to the photodiode, arrayed two-dimensionally in M rows and N columns;
a row selection line $L_{V,m}$ applying an m-th row selection control signal for instructing an opening and closing operation to the readout switch of each of N pixels $P_{m,1}$ to $P_{m,N}$ in an m-th row in the photodetecting unit;
a readout line $L_{O,n}$ being connected to the readout switch of each of M pixels $P_{1,n}$ to $N_{M,n}$ in an n-th column in the photodetecting unit, and reading the charge generated in the photodiode of any of the M pixels $P_{1,n}$ to $P_{M,n}$ via the readout switch of the pixel;
an output unit being connected to each of the readout lines $L_{O,1}$ to $L_{O,N}$ and outputting a digital value generated on the basis of the amount of the charge input via the readout line $L_{O,n}$; and a control unit controlling an opening and closing operation of the readout switch of each of MN pixels $P_{1,1}$ to $P_{M,N}$ in the photodetecting unit via the row selection lines $L_{V,1}$ to $L_{V,M}$ and controlling a digital value output operation in the output unit, wherein the control unit divides the pixels $P_{1,1}$ to $P_{M,N}$ arrayed two-dimensionally in M rows and N columns in the photodetecting unit into unit regions each including pixels in Q rows and R columns, divides the unit regions arrayed two-dimensionally in (M/Q) rows and (N/R) columns into binning regions each including unit regions in K rows and one column, closes the readout switches of the pixels included in the binning region in the row for each row sequentially for the binning regions arrayed two-dimensionally in (M/KQ) rows and (N/R) columns in the photodetecting unit, inputs the charges generated in the photodiodes of the pixels to the output unit, and repeatedly outputs the digital value according to the sum of amounts of the charges output from the KQR pixels included in each binning region from the output unit K times sequentially for each column (where M and N are each an integer of 2 or more, m is an integer of 1 or more and M or less, n is an integer of 1 or more and N or less, Q and R are each an integer of 1 or more, and K is an integer of 2 or more).

2. The solid-state imaging device according to claim 1, wherein the output unit includes a storage unit storing the digital value according to the sum of amounts of the charges output from the pixels included in each binning region, and the control unit repeatedly reads and outputs the digital value stored in the storage unit from the storage unit K times sequentially for each column.

3. The solid-state imaging device according to claim 2, wherein the output unit includes, as the storage unit, K FIFO memories storing the digital value according to the sum of amounts of the charges output from the pixels included in each binning region sequentially for each column, and the control unit causes the digital values to be sequentially output from the K FIFO memories so that the digital value according to the sum of amounts of the charges output from the pixels included in each binning region is repeatedly output K times sequentially for each column.

4. The solid-state imaging device according to claim 2, wherein the output unit includes, as the storage unit, a FIFO memory storing the digital value according to the sum of amounts of the charges output from the pixels included in each binning region sequentially for each column, and the control unit causes the digital value to be output from the FIFO memory and causes the digital value to be stored in the FIFO memory so that the digital value according to the sum of amounts of the charges output from the pixels included in each binning region is repeatedly output K times sequentially for each column.

5. The solid-state imaging device according to claim 1, comprising a plurality of blocks each including the photodetecting unit and the output unit connected to each other by the readout line $L_{O,n}$, wherein the photodetecting units in the respective blocks are arranged in parallel in the row direction.

6. An X-ray imaging system comprising:

the solid-state imaging device according to claim 1, and an X-ray generating device, wherein X-rays output from the X-ray generating device and transmitted through an imaging object are imaged by the solid-state imaging device.

7. The X-ray imaging system according to claim 6, wherein the solid-state imaging device moves in the column direction in the photodetecting unit in the imaging period.

8. A method for driving a solid-state imaging device including:

a photodetecting unit including MN pixels $P_{1,1}$ to $P_{M,N}$, each including a photodiode generating a charge of an amount according to an incident light intensity and a readout switch connected to the photodiode, arrayed two-dimensionally in M rows and N columns;

a row selection line $L_{V,m}$ applying an m-th row selection control signal for instructing an opening and closing operation to the readout switch of each of N pixels $P_{m,1}$ to $P_{m,N}$ in an m-th row in the photodetecting unit;

a readout line $L_{O,n}$ being connected to the readout switch of each of M pixels $P_{1,n}$ to $P_{M,n}$ in an n-th column in the photodetecting unit, and reading the charge generated in the photodiode of any of the M pixels $P_{1,n}$ to $P_{M,n}$ via the readout switch of the pixel; and an output unit being connected to each of the readout lines $L_{O,1}$ to $L_{O,N}$ and outputting a digital value generated on the basis of the amount of the charge input via the readout line $L_{O,n}$, the solid-state imaging device driving method comprising:

dividing the pixels $P_{1,1}$ to $P_{M,N}$ arrayed two-dimensionally in M rows and N columns in the photodetecting unit into unit regions each including pixels in Q rows and R columns, dividing the unit regions arrayed two-dimensionally in (M/Q) rows and (N/R) columns into binning regions each including unit regions in K rows and one column, closing the readout switches of the pixels included in the binning region in the row for each row sequentially for the binning regions arrayed two-dimensionally in (M/KQ) rows and (N/R) columns in the photodetecting unit, inputting the charges generated in the photodiodes of the pixels to the output unit, and repeatedly outputting the digital value according to the sum of amounts of the charges output from the KQR pixels included in each binning region from the output unit K times sequentially for each column (where M and N are each an integer of 2 or more, m is an integer of 1 or more and M or less, n is an integer of 1 or more and N or less, Q and R are each an integer of 1 or more, and K is an integer of 2 or more).

9. The solid-state imaging device driving method according to claim 8, wherein in the output unit, a storage unit storing the digital value according to the sum of amounts of the charges output from the pixels included in each binning region is used, and the digital value stored in the storage unit is repeatedly read and output from the storage unit K times sequentially for each column.

10. The solid-state imaging device driving method according to claim 9, wherein in the output unit, as the storage unit, K FIFO memories storing the digital value according to the sum of amounts of the charges output from the pixels included in each binning region sequentially for each column are used, and the digital values are sequentially output from the K FIFO memories so that the digital value according to the sum of amounts of the charges output from the pixels included in each binning region is repeatedly output K times sequentially for each column.

11. The solid-state imaging device driving method according to claim 9, wherein in the output unit, as the storage unit, a FIFO memory storing the digital value according to the sum of amounts of the charges output from the pixels included in each binning region sequentially for each column is used, and the digital value is output from the FIFO memory and the digital value is stored in the FIFO memory so that the digital value according to the sum of amounts of the charges output from the pixels included in each binning region is repeatedly output K times sequentially for each column.

* * * * *